(12) United States Patent
Goepfert et al.

(10) Patent No.: US 8,314,225 B2
(45) Date of Patent: Nov. 20, 2012

(54) HEAVY CHAIN MUTANT LEADING TO IMPROVED IMMUNOGLOBULIN PRODUCTION

(75) Inventors: Ulrich Goepfert, Munich (DE); Silke Hansen, Iffeldorf (DE); Hendrik Knoetgen, Penzberg (DE); Erhard Kopetzki, Penzberg (DE); Oliver Ploettner, Munich (DE)

(73) Assignee: Hoffman-La Roche Inc., Nutley, NJ (US)

( * ) Notice: Subject to any disclaimer, the term of this patent is extended or adjusted under 35 U.S.C. 154(b) by 402 days.

(21) Appl. No.: 12/664,401

(22) PCT Filed: Jun. 25, 2008

(86) PCT No.: PCT/EP2008/005136
§ 371 (c)(1),
(2), (4) Date: Dec. 14, 2009

(87) PCT Pub. No.: WO2009/003623
PCT Pub. Date: Jan. 8, 2009

(65) Prior Publication Data
US 2010/0184144 A1 Jul. 22, 2010

(30) Foreign Application Priority Data
Jun. 29, 2007 (EP) .................... 07012774

(51) Int. Cl.
*C07H 21/04* (2006.01)
(52) U.S. Cl. .................... 536/23.53
(58) Field of Classification Search .................. None
See application file for complete search history.

(56) References Cited

U.S. PATENT DOCUMENTS

| | | | |
|---|---|---|---|
| 5,202,238 A | 4/1993 | Fell, Jr. et al. | |
| 5,204,244 A | 4/1993 | Fell et al. | |
| 5,888,809 A | 3/1999 | Allison | |
| 2005/0008642 A1 | 1/2005 | Graus et al. | |
| 2005/0226876 A1 | 10/2005 | Graus et al. | |
| 2006/0099206 A1 | 5/2006 | Sinacore et al. | |
| 2009/0232823 A1* | 9/2009 | Balderes et al. | 424/139.1 |

FOREIGN PATENT DOCUMENTS

| | | |
|---|---|---|
| EP | 1646720 | 4/2006 |
| WO | WO 92/08796 | 5/1992 |
| WO | WO 94/28143 | 12/1994 |
| WO | WO 02/16944 | 2/2002 |
| WO | WO 2005/100402 | 10/2005 |
| WO | WO 2006/042158 | 4/2006 |
| WO | 2006/122822 | 11/2006 |
| WO | 2006/126068 | 11/2006 |
| WO | 2006/126069 | 11/2006 |

OTHER PUBLICATIONS

European Office Action dated Sep. 1, 2010 in European Appl. EP 08773643.5.
Database EMBL [Online] (2005) XP002458130 retrieved from EBI accession No. EMBL:DB343679 Database accession No. DB343679.
Database EMBL [Online] (2000) XP002458131 retrieved from EBI accession No. EMBL:AW394005 Database accession No. AW394005.
Brown S. L. et al.—*Journal of Immunology*, 142:2072-2080, (1989).
Khamlichi A. et al.—*Gene*, 150:387-390 (1994).
Danner D. et al.—*Proceedings of the National Academy of Sciences*, 82:8658-8662 (1985).
Adam, M. et al, *Jour. Virol.* 65 (1991) 4985-4990.
Ausubel, F. *Current Protocols in Molecular Biology*, vol. I-III (1997).
Banerji, J. et al, *Cell*, 33 (1983) 729-740.
Bonifacino,J. et al, *Current Protocols in cell Biology*, (2000).
Davies, M. et al, *J. Virol.* 66:1924-1932 (1992).
Geisse, S. et al, *Protein Expr. Purif*, 8:271-282 (1996).
Gossen, M., *PNAS* 89 (1992) 5547-5551.
Gossen, M., *Curr. Opin Biotech* 5:516-520 (1994).
Jang, S. et al . *Virol.* 63:1651-1660 (1989).
Kaufman, R. *Mol. Biotechnol* 16:151-160 (2000).
Lemaigre, F. et al, *Biochem. J*, 303:1-14 (1994).
Loeken, M. *Gene Expr.* 3 (1993) 253.
Lusky, M. et al, *Mol. Cell Bio*, 3:1108-1122 (1983).
Makrides, S., *Protein Expr. Purif*, 17:183-202 (1999).
McGehee,R. et al ,*Mol. Endocrinol*, 7:551-560 (1993).
Morgan, R. et al, *Nucl. Acids Res*, 20:1293-1299 (1992).
Morrison, S. et al, *Proc. Natal. Acad. Sci* 81:6851-6855 (1984).
Mosser, D.et al, *BioTechniques* 22:150-161 (1997).
Osborne, T. et al, *Mol. Cell Bio*, 4:1293-1305 (1984).
Pelletier, J. et al, *Nature* 334:320-325 (1988).
Ramesh, N. et al, *Nucl. Acids Res* 24:2697-2700 (1996).
Sambrook et al, *Molecular Cloning: A Laboratory Manual*, 2$^{nd}$ Ed (1989) Cold Spring Harbor Lab Press.
Sugimoto, Y et al, *Biotech* 12:694-698 (1994).
Treisman, R. *Seminars in Cancer Biol* 1:47-58 (1990).
Watson et al, *Recombinant DNA: A Short course*, Scientific Amer. Books (1983).
Werner, R. *Drug Research* 48:870-880 (1998).
Strausberg, R. et al., Proc Natl Acad. Sci. USA 4(99):16899-16903 (Dec. 11, 2002).
(Database (online) Accession No. BC073767 Jun. 29, 2004).
(Taiwanese Search Report Corres. to Taiwan Pat. Appl. 097124423 Mar. 9, 2011).
(Database EMBL (online) Accession No. BC073765 Jun. 29, 2004).
GENBANK AJ390247.1 Feb. 5, 2012.
GENBANK AJ250170.1 Feb. 5, 2012.
GENBANK X67301.1 Feb. 5, 2012.
Translation Russian Off Act in Corres Russian Appl 102811 Feb. 17, 2012).
GENBANK S64472.1 Feb. 5, 2012.
GENBANK DQ487208 Feb. 5, 2012.
Jarygin, V.N. et al., Biology 2:68-71 ( 1997).
GENBANK AY372690.1 Feb. 5, 2012.
GENBANK AF4873336 Feb. 5, 2012.
GENBANK AY647979.1 Feb. 5, 2012.

* cited by examiner

*Primary Examiner* — Ilia Ouspenski
(74) *Attorney, Agent, or Firm* — George W. Johnston; Dennis P. Tramaloni; Brian C. Remy

(57) ABSTRACT

The current invention comprises a nucleic acid encoding the amino acid sequence of the C-terminal part of the $C_H3$-domain of an immunoglobulin of the class IgA or IgG, or the C-terminal part of the $C_H4$-domain of an immunoglobulin of the class IgE or IgM, wherein the glycine-lysine-dipeptide comprised in the amino acid sequence of the C-terminal part of the $C_H3$- or $C_H4$-domain is encoded by the nucleic acid ggaaaa, or the nucleic acid ggcaaa, or the nucleic acid gggaaa, or the nucleic acid gggaag, or the nucleic acid ggcaag, or the nucleic acid ggaaag.

20 Claims, 7 Drawing Sheets

HEAVY CHAIN MUTANT LEADING TO IMPROVED IMMUNOGLOBULIN PRODUCTION

This application is the National Stage of International Application No. PCT/EP2008/005136 filed Jun. 25, 2008, which claims the benefit of EP 07012774.1 filed Jun. 29, 2007, which is hereby incorporated by reference in its entirety.

The current application describes methods and nucleic acids useful in the production of immunoglobulins in mammalian cells.

BACKGROUND OF THE INVENTION

Expression systems for the production of recombinant polypeptides are well-known and reported in the state of the art literature. For the production of polypeptides used in pharmaceutical applications mammalian cells such as CHO cells, BHK cells, NS0 cells, Sp2/0 cells, COS cells, HEK cells, PER.C6® cells, and the like are employed. The nucleic acid encoding the polypeptide is introduced into the cell e.g. in a plasmid, such as, for example, an expression plasmid. The essential elements of an expression plasmid are a prokaryotic plasmid propagation unit, e.g. for *Escherichia coli* comprising an origin of replication and a selection marker, a eukaryotic selection marker, and one or more expression cassettes for the expression of the nucleic acid(s) of interest each of them comprising a promoter, a structural gene, and a transcription terminator including a polyadenylation signal. For transient expression in mammalian cells a mammalian origin of replication, such as the SV40 Ori or OriP, may be included. As a promoter a constitutive or inducible promoter can be selected. For optimized transcription a Kozak sequence may be included in the 5' untranslated region. For mRNA processing a polyadenylation signal may be included as well.

Proteins and especially immunoglobulins play an important role in today's medical portfolio. For human application every pharmaceutical substance has to meet distinct criteria. To ensure the safety of biopharmaceutical agents to humans substances, which would cause severe harm, have to be removed especially.

The splicing of mRNA is regulated by the occurrence of a splice donor site in combination with a splice acceptor site, which are located at the 5' end and 3' end of an intron, respectively. According to Watson et al. (Watson et al. (Eds), Recombinant DNA: A Short course, Scientific American Books, distributed by W.H. Freeman and Company, New York, N.Y., USA (1983)) are the consensus sequence of the 5' splice donor site ag|gtragt (exon|intron) and of the 3'splice acceptor site (y)$_n$Ncag|g (intron|exon) (r=purine base; y=pyrimidine base; n=integer; N=any natural base).

In 1980 first articles dealing with the origin of secreted and membrane bound forms of immunoglobulins have been published. The formation of the secreted (sIg) and the membrane bound (mIg) isoform results from alternative splicing of the heavy chain pre-mRNA. In the mIg isoform a splice donor site in the exon encoding the C-terminal domain of the secreted form (i.e. the $C_H3$ or $C_H4$ domain, respectively) and a splice acceptor site located at a distance downstream thereof are used to link the constant region with the downstream exons encoding the transmembrane domain.

A method to prepare synthetic nucleic acid molecules having reduced inappropriate or unintended transcriptional characteristics when expressed in a particular host cell is reported in WO 2002/016944. In WO 2006/042158 are reported nucleic acid molecules modified to enhance recombinant protein expression and/or reduce or eliminate mis-spliced and/or intron read through by products.

Therefore there exists a need for a recombinant production method for immunoglobulins with reduced by products.

SUMMARY OF THE INVENTION

The current invention comprises in a first aspect a nucleic acid encoding the amino acid sequence of the C-terminal part of the $C_H3$-domain of an immunoglobulin of the class IgA or IgG, or the C-terminal part of the $C_H4$-domain of an immunoglobulin of the class IgE or IgM, wherein the glycine-lysine-dipeptide comprised in the primary amino acid sequence of the C-terminal part of the $C_H3$- or $C_H4$-domain is encoded by the nucleic acid ggaaaa, or the nucleic acid ggcaaa, or the nucleic acid gggaaa, or the nucleic acid ggaaag, or the nucleic acid ggcaag, or the nucleic acid gggaag.

In one embodiment the nucleic acid according to the invention encodes an amino acid sequence selected from the amino acid sequences SEQ ID NO: 1, 3, 4, 5, 6, 7, or 8. In another embodiment is the nucleic acid encoding the glycine-lysine-dipeptide preceded by the nucleotide g or a. In another embodiment is the nucleic acid encoding the glycine-lysine-dipeptide the nucleic acid ggaaaa, or the nucleic acid ggcaaa, or the nucleic acid gggaaa.

The second aspect of the current invention is a plasmid comprising the nucleic acid according to the invention, and the third aspect of the invention is a cell comprising the nucleic acid according to the invention.

A further aspect of the invention is a nucleic acid with the nucleotide sequence of SEQ ID NO: 17, 18, 19, 20, 21, 22, 23, 30, or 31.

The fifth aspect of the invention is a method for the production of an immunoglobulin in a mammalian cell comprising the following steps:
a) transfecting a mammalian cell with a nucleic acid encoding an immunoglobulin heavy chain comprising a nucleic acid of SEQ ID NO: 17, 18, 19, 20, 21, 22, 23, 30, or 31, which encodes the C-terminal part of the immunoglobulin heavy chain,
b) cultivating the transfected mammalian cell under conditions suitable for the expression of the immunoglobulin,
c) recovering the immunoglobulin from the culture or the cell.

In one embodiment is the mammalian cell a CHO cell, a BHK cell, a NS0 cell, a Sp2/0 cell, a COS cell, a HEK cell, or a PER.C6® cell. Preferably the mammalian cell is a CHO cell, or a BHK cell, or a PER.C6® cell. In another embodiment is the mammalian cell transfected with two nucleic acids, wherein the first nucleic acid comprises an expression cassette encoding an immunoglobulin light chain, and wherein the second nucleic acid comprises an expression cassette encoding an immunoglobulin heavy chain comprising a nucleic acid of SEQ ID NO: 17, 18, 19, 20, 21, 22, 23, 30, or 31 encoding the C-terminal part of the immunoglobulin heavy chain.

The final aspect of the invention is a method for improving the expression of an immunoglobulin in a mammalian cell, wherein the nucleic acid encoding the immunoglobulin heavy chain comprises the nucleic acid ggaaaa, or the nucleic acid ggcaaa, or the nucleic acid gggaaa, or the nucleic acid ggaaag, or the nucleic acid ggcaag, or the nucleic acid gggaag encoding the glycine-lysine-dipeptide contained in the $C_H3$- or $C_H4$-domain.

DETAILED DESCRIPTION OF THE INVENTION

The current invention comprises a nucleic acid encoding the amino acid sequence of the C-terminal part of the $C_H3$- domain of an immunoglobulin of the class IgA or IgG, or the C-terminal part of the $C_H4$-domain of an immunoglobulin of the class IgE or IgM, wherein the glycine-lysine-dipeptide comprised in the amino acid sequence of the C-terminal part of the $C_H3$- or $C_H4$-domain is encoded by the nucleic acid ggaaaa, or the nucleic acid ggcaaa, or the nucleic acid gggaaa, or the nucleic acid ggaaag, or the nucleic acid ggcaag, or the nucleic acid gggaag, and wherein the nucleic acid encoding the glycine-lysine-dipeptide is optionally preceded either by the nucleotide g or the nucleotide a.

Methods and techniques useful for carrying out the current invention are known to a person skilled in the art and are described e.g. in Ausubel, F. M., ed., Current Protocols in Molecular Biology, Volumes I to III (1997), and Sambrook et al., Molecular Cloning: A Laboratory Manual, Second Edition, Cold Spring Harbor Laboratory Press, Cold Spring Harbor, N.Y. (1989). As known to a person skilled in the art enables the use of recombinant DNA technology the production of numerous derivatives of a nucleic acid and/or polypeptide. Such derivatives can, for example, be modified in one individual or several positions by substitution, alteration, exchange, deletion, or insertion. The modification or derivatisation can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA). The use of recombinant technology enables a person skilled in the art to transform various host cells with heterologous nucleic acid(s). Although the transcription and translation, i.e. expression, machinery of different cells use the same elements, cells belonging to different species may have among other things a different so-called codon usage. Thereby identical polypeptides (with respect to amino acid sequence) may be encoded by different nucleic acid(s). Also, due to the degeneracy of the genetic code, different nucleic acids may encode the same polypeptide.

A "nucleic acid" as used herein, refers to a polymeric molecule consisting of the individual nucleotides (also called bases) a, c, g, and t (or u in RNA), for example to DNA, RNA, or modifications thereof. This polynucleotide molecule can be a naturally occurring polynucleotide molecule or a synthetic polynucleotide molecule or a combination of one or more naturally occurring polynucleotide molecules with one or more synthetic polynucleotide molecules. Also encompassed by this definition are naturally occurring polynucleotide molecules in which one or more nucleotides are changed (e.g. by mutagenesis), deleted, or added. A nucleic acid can either be isolated, or integrated in another nucleic acid, e.g. in an expression cassette, a plasmid, or the chromosome of a host cell. A nucleic acid is likewise characterized by its nucleic acid sequence consisting of individual nucleotides.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

The term "plasmid" includes e.g. shuttle and expression plasmids as well as transfection plasmids. The term "vector" is used synonymously for "plasmids" within this application. Typically, a "plasmid" will also comprise an origin of replication (e.g. the ColE1 or oriP origin of replication) and a selection marker (e.g. an ampicillin, kanamycin, tetracycline, or chloramphenicol selection marker), for replication and selection, respectively, of the plasmid in bacteria.

An "expression cassette" refers to a construct that contains the necessary regulatory elements, such as promoter and polyadenylation site, for expression of at least the contained nucleic acid in a cell.

A "selection marker" is a nucleic acid that allows cells carrying the selection marker to be specifically selected for or against, in the presence of a corresponding selection agent. Typically, a selection marker will confer resistance to a drug or compensate for a metabolic or catabolic defect in the host cell. A selection marker can be positive, negative, or bifunctional. A useful positive selection marker is an antibiotic resistance gene. This selection marker allows the host cell transformed therewith to be positively selected for in the presence of the corresponding selection agent, e.g. the antibiotic. A non-transformed host cell is not capable to grow or survive under the selective culture conditions, i.e. in the presence of the selection agent, in the culture. Positive selection markers allow selection for cells carrying the marker, whereas negative selection markers allow cells carrying the marker to be selectively eliminated. Selection markers used with eukaryotic cells include, e.g., the genes for aminoglycoside phosphotransferase (APH), such as e.g. the hygromycin (hyg), neomycin (neo), and G418 selection markers, dihydrofolate reductase (DHFR), thymidine kinase (tk), glutamine synthetase (GS), asparagine synthetase, tryptophan synthetase (selection agent indole), histidinol dehydrogenase (selection agent histidinol D), and nucleic acids conferring resistance to puromycin, bleomycin, phleomycin, chloramphenicol, Zeocin, and mycophenolic acid. Further marker genes are reported e.g. in WO 92/08796 and WO 94/28143.

The term "expression" as used herein refers to transcription and/or translation processes occurring within a cell. The level of transcription of a nucleic acid sequence of interest in a cell can be determined on the basis of the amount of corresponding mRNA that is present in the cell. For example, mRNA transcribed from a sequence of interest can be quantitated by RT-PCR or by Northern hybridization (see Sambrook et al., 1989, supra). Polypeptides encoded by a nucleic acid of interest can be quantitated by various methods, e.g. by ELISA, by assaying for the biological activity of the polypeptide, or by employing assays that are independent of such activity, such as Western blotting or radioimmunoassay, using immunoglobulins that recognize and bind to the polypeptide (see Sambrook et al., 1989, supra).

The term "cell" or "host cell" refers to a cell into which a nucleic acid, e.g. encoding a heterologous polypeptide, can be or is introduced/transfected. The term "cell" includes both prokaryotic cells, which are used for propagation of plasmids, and eukaryotic cells, which are used for the expression of a nucleic acid. Preferably, the eukaryotic cells are mammalian cells. Preferably the mammalian cell is selected from the group of mammalian cells comprising CHO cells (e.g. CHO K1, CHO DG44), BHK cells, NS0 cells, SP2/0 cells, HEK 293 cells, HEK 293 EBNA cells, PER.C6® cells, and COS cells. As used herein, the expression "cell" includes the subject cell and its progeny. Thus, the words "transformant" and "transformed cell" include the primary subject cell and cells in cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "amino acid" as used within this application denotes a group of carboxy α-amino acids, which directly or in form of a precursor can be encoded by a nucleic acid. The individual amino acids are encoded by nucleic acids each consisting of three nucleotides, so called codons or base-triplets. Each amino acid is encoded by at least one codon. For example the amino acid glycine can be encoded by each of the four nucleic acids (codons) gga, ggc, ggg, and ggt, whereas the amino acid lysine can only be encoded by the two nucleic acids aaa, and aag. This phenomenon is known as "degeneration of the genetic code". The group of amino acids comprises alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

As used herein, the term "immunoglobulin" denotes a protein consisting of one or more polypeptides substantially encoded by immunoglobulin genes. This definition includes variants such as mutated forms, i.e. forms with substitutions, deletions, and insertions of one or more amino acids, N-terminally truncated forms, fused forms, chimeric forms, as well as humanized forms. The recognized immunoglobulin genes include the different constant region genes as well as the myriad immunoglobulin variable region genes from, e.g., primates and rodents. Monoclonal immunoglobulins are preferred. Each of the heavy and light polypeptide chains of an immunoglobulin may comprise a constant region (generally the carboxyl terminal portion).

The term "monoclonal immunoglobulin" as used herein refers to an immunoglobulin obtained from a population of substantially homogeneous immunoglobulins, i.e. the individual immunoglobulins comprising the population are identical except for possible naturally occurring mutations that may be present in minor amounts. Monoclonal immunoglobulins are highly specific, being directed against a single antigenic site. Furthermore, in contrast to polyclonal immunoglobulin preparations, which include different immunoglobulins directed against different antigenic sites (determinants or epitopes), each monoclonal immunoglobulin is directed against a single antigenic site on the antigen. In addition to their specificity, the monoclonal immunoglobulins are advantageous in that they may be synthesized uncontaminated by other immunoglobulins. The modifier "monoclonal" indicates the character of the immunoglobulin as being obtained from a substantially homogeneous population of immunoglobulins and is not to be construed as requiring production of the immunoglobulin by any particular method.

"Humanized" forms of non-human (e.g. rodent) immunoglobulins are chimeric immunoglobulins that contain partial sequences derived from non-human immunoglobulin and from human immunoglobulin. For the most part, humanized immunoglobulins are derived from a human immunoglobulin (recipient immunoglobulin), in which residues from a hypervariable region are replaced by residues from a hypervariable region of a non-human species (donor immunoglobulin), such as mouse, rat, rabbit, or non-human primate, having the desired specificity and affinity (see e.g. Morrison, S. L., et al., Proc. Natal. Acad. Sci. USA 81 (1984) 6851-6855; U.S. Pat. Nos. 5,202,238; 5,204,244). In some instances, framework region (FR) residues of the human immunoglobulin are replaced by corresponding non-human residues. Furthermore, humanized immunoglobulins may comprise further modifications, e.g. amino acid residues that are not found in the recipient immunoglobulin or in the donor immunoglobulin. Such modifications result in variants of such recipient or donor immunoglobulin, which are homologous but not identical to the corresponding parent sequence. These modifications are made to further refine immunoglobulin performance. In general, the humanized immunoglobulin will comprise substantially all of at least one, and typically two, variable domains, in which all or substantially all of the hypervariable loops correspond to those of a non-human donor immunoglobulin and all or substantially all of the FRs are those of a human recipient immunoglobulin. The humanized immunoglobulin optionally will also comprise at least a portion of an immunoglobulin constant region, typically that of a human immunoglobulin. Methods for humanizing non-human immunoglobulin have been described in the art. Preferably, a humanized immunoglobulin has one or more amino acid residues introduced into it from a source which is non-human. These non-human amino acid residues are often referred to as "import" residues, which are typically taken from an "import" variable domain. Humanization can be essentially performed following the method of Winter and co-workers by substituting hypervariable region sequences for the corresponding sequences of a non-human immunoglobulin. Accordingly, such "humanized" immunoglobulins are chimeric immunoglobulins, wherein substantially less than an intact human variable domain has been substituted by the corresponding sequence from a non-human species. In practice, humanized immunoglobulins are typically human immunoglobulins in which some hypervariable region residues and possibly some framework region residues are substituted by residues from analogous sites in rodent or non-human primate immunoglobulins.

Depending on the amino acid sequence of the constant region of their heavy chains, immunoglobulins are divided in the classes: IgA, IgD, IgE, IgG, and IgM. Some of these may be further divided into subclasses (isotypes), e.g. IgG1, IgG2, IgG3, and IgG4, IgA1 and IgA2. According to the heavy chain constant regions the different classes of immunoglobulins heavy chains are denoted as α-, δ-, ε-, γ-, and μ-chain respectively. The constant region of a heavy chain of a full length human immunoglobulin of the class IgA, IgD, and IgG is constituted of a constant domain 1 (herein denoted as $C_H1$), a hinge region, a constant domain 2 ($C_H2$), and a constant domain 3 ($C_H3$). Human immunoglobulins of the class IgE and IgM comprise an additional fourth constant domain ($C_H4$). Furthermore are immunoglobulins of the class IgM polymers comprising multiple immunoglobulins, e.g. five or six, covalently linked by disulfide bonds. The C-terminal constant domain amino acid sequence of these different human immunoglobulin classes are listed in Table 1. The first amino acid of SEQ ID NO: 01 to 08 may be present or not, because this amino acid is encoded by two exons, the exon encoding the C-terminal constant domain and the exon encoding the preceding domain.

TABLE 1

C-terminal amino acid sequence of the different immunoglobulin classes. The glycine-lysine-dipeptides are underlined.

| immunoglobulin class (C-terminal constant domain) | amino acid sequence of the C-terminal part (in N-terminal to C-terminal direction) | SEQ ID NO: |
|---|---|---|
| IgA1 ($C_H3$), IgA2 ($C_H3$) | GNTFRPEVHL LPPPSEELAL NELVTLTCLA RGFSPKDVLV RWLQGSQELP REKYL TWASR QEPSQGTTTF AVTSILRVAA EDWKKGDTFS CMVGHEALPL AFTQK TIDRL A<u>GK</u>PTHVNVS VVMAEVDGTC Y | 01 |
| IgD ($C_H3$) | AAQAPVKLSLN LLASSDPPEA ASWLLCEVSG FSPPNILLMW LEDQREVNTS GFAPARPPPQ PGSTTFWAWS VLRVPAPPSP QPATYTCVVS HEDSRTLLNA SRSLEVSY | 02 |
| IgE ($C_H4$) | GPRAAPEVYA FATPEWPGSR DKRTLACLIQ NFMPEDISVQ WLHNEVQLPD ARHSTTQPRK TKGSGFFVFS RLEVTRAEWE QKDEFICRAV HEAASPSQTV QRAVSVNP<u>GK</u> | 03 |
| IgM ($C_H4$) | GVALHRPDVY LLPPAREQLN LRESATITCL VTGFSPADVF VQWMQRGQPL SPEKYVTSAP MPEPQAPGRY FAHSILTVSE EEWNTGETYT CVVAHEALPN RVT ERTVDK ST<u>GK</u>PTLYNV SLVMSDTAGT CY | 04 |
| IgG1 ($C_H3$) | GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSP<u>GK</u> | 05 |
| IgG2 ($C_H3$) | GQPREPQVYT LPPSREEMTK NQVSLTCLVK GFYPSDIAVE WESNGQPENN YKTTPPMLDS DGSFFLYSKL TVDKSRWQQG NVFSCSVMHE ALHNHYTQKS LSLSP<u>GK</u> | 06 |
| IgG3 ($C_H3$) | GQPREPQVYT LPPSREEMTK NQVSLTCLVK GFYPSDIAVE WESSGQPENN YNTTPPMLDS DGSFFLYSKL TVDKSRWQQG NIFSCSVMHE ALHNRFTQKS LSLSP<u>GK</u> | 07 |
| IgG4 ($C_H3$) | GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSL<u>GK</u> | 08 |

The term "C-terminal part of the $C_H3$-domain of an immunoglobulin of the class IgA or IgG, or the C-terminal part of the $C_H4$-domain of an immunoglobulin of the class IgE or IgM" denotes the amino acid sequences of an immunoglobulin heavy chain, which is located at the C-terminal end of a full-length or naturally occurring immunoglobulin heavy chain, whereby the C-terminus of said C-terminal part is identical to the C-terminus of the primary amino acid sequence of the immunoglobulin heavy chain. The term "primary amino acid sequence" denotes the amino acid sequence of an immunoglobulin heavy chain after the translation of the corresponding mRNA. This primary amino acid sequence may further be modified in the expressing cell after the mRNA translation e.g. by peptidases cleaving one or more C-terminal amino acids from the primary amino acid sequence. Therefore the primary amino acid sequence and the secreted amino acid sequence may not be identical but may differ by some amino acids at the C-terminus. In one embodiment the C-terminal part comprises at least the 100 C-terminal amino acids of an immunoglobulin heavy chain primary amino acid sequence, or preferably at least the 50 C-terminal amino acids of an immunoglobulin heavy chain primary amino acid sequences, or preferably the at least 20 C-terminal amino acids of an immunoglobulin heavy chain primary amino acid sequence. In one embodiment the nucleic acid according to the invention is encoding the amino acid sequence of the C-terminal part of the $C_H3$-domain of an immunoglobulin of the class IgG, or the C-terminal part of the $C_H4$-domain of an immunoglobulin of the class IgE. In a further embodiment the nucleic acid according to the invention is encoding the amino acid sequence of the C-terminal part of the $C_H3$ domain of an immunoglobulin of the class IgG.

The C-terminal constant domain amino acid sequences of the different human immunoglobulins are encoded by corresponding DNA sequences. In the genome these DNA sequences contain coding (exonic) and non-coding (intronic) sequences. After transcription of the DNA to the pre-mRNA the pre-mRNA also contains these intronic and exonic sequences. Prior to translation the non-coding intronic sequences are removed during mRNA processing by splicing them out of the primary mRNA transcript to generate the mature mRNA. The splicing of the primary mRNA is controlled by a splice donor site in combination with a properly spaced apart splice acceptor site. The splice donor site is located at the 5' end and the splice acceptor site is located at the 3' end of an intronic sequence and both are partly removed during the pre-mRNA splicing process.

The term "properly spaced apart" denotes that a splice donor site and a splice acceptor site in a nucleic acid are arranged in such a way that all required elements for the splicing process are available and are in an appropriate position to allow the splicing process to take place.

The current invention comprises a nucleic acid encoding the amino acid sequence of the C-terminal part of the $C_H3$-domain of an immunoglobulin of the class IgA or IgG, or the C-terminal part of the $C_H4$-domain of an immunoglobulin of the class IgE or IgM, wherein the glycine-lysine-dipeptide comprised in said amino acid sequence of the C-terminal part of the $C_H3$- or $C_H4$-domain is encoded by the nucleic acid ggaaaa, or the nucleic acid ggcaaa, or the nucleic acid gggaaa.

It has been surprisingly found that with the nucleic acid according to the invention unwanted by product formation by unwanted splicing events can be reduced.

The term "glycine-lysine-dipeptide" as used within the current application denotes the peptide comprising in N-terminal to C-terminal direction the two amino acids glycine and lysine linked by a peptide bond. The term "glycine-lysine-dipeptide" as used within this application denotes a dipeptide fraction of a larger polypeptide or protein, which can be found at the beginning, within, or at the end of the larger polypeptide. The amino acid lysine can be encoded by the nucleic acids aaa and aag. Therefore it is another embodiment of the current invention that the glycine-lysine-dipeptide comprised in the amino acid sequence of the C-terminal part of the $C_H3$- or $C_H4$-domain of an immunoglobulin heavy chain is encoded by the nucleic acid ggaaag, or the nucleic acid ggcaag, or the nucleic acid gggaag. In another embodiment the nucleic acid encoding the glycine-lysine-dipeptide is preceded by the nucleotide a or g.

Nucleic acid sequences encoding the C-terminal constant domain of different human immunoglobulin classes and subclasses are listed in Table 2. For the $C_H3$ domain of human IgG1 and IgG2 two variant forms are known. In one embodiment encodes the nucleic acid a part of the C-terminal constant domain of an immunoglobulin heavy chain.

TABLE 2

Nucleic acid sequences encoding the C-terminal part of the heavy chain of the different human immunoglobulin classes.

| immunoglobulin class (C-terminal constant domain) | nucleic acid sequence encoding the C-terminal part of the amino acid sequence of an immunoglobulin heavy chain | SEQ ID NO: |
|---|---|---|
| IgA1 ($C_H3$), IgA2 ($C_H3$) | ggcttcagcc ccaaggacgt gctggttcgc tggctgcagg ggtcacagga gctgccccgc gagaagtacc tgacttgggc atcccggcag gagcccagcc agggcaccac caccttcgct gtgaccagca tactgcgcgt ggcagccgag gactggaaga aggggacac cttctcctgc atggtggcc acgaggcct gccgctggcc ttcacacaga agaccatcga ccgcttggcg ggtaaaccca cccatgtcaa tgtgtctgtt gtcatggcgg aggtggacgg cacctgctac | 09 |
| IgD ($C_H3$) | taccacccaa cgtccgtgac tgtcacctgg tacatgggga cacagagcca gccccagaga accttccctg agatacaaag acgggacagc tactacatga caagcagcca gctctccacc cccctccagc agtggcgcca aggcgagtac aaatgcgtgg tccagcacac cgccagcaag agtaagaagg agatcttccg ctggcaggt aggtcgcacc ggagatcacc cagaagggcc ccccaggacc cccagcacct tccactcagg gcctgaccac aaagacagaa gcaagggctg | 10 |
| IgE ($C_H4$) | tttgcgacgc cggagtggc ggggagccgg gacaagcgca ccctcgcctg cctgatccag aacttcatgc ctgaggacat ctcggtgcag tggctgcaca acgaggtgca gctcccggac gcccggcaca gcacgacga gccccgcaag accaagggct ccggcttctt cgtcttcagc cgcctggagg tgaccagggc cgaatgggag cagaaagatg agttcatctg ccgtgcagtc catgaggcag cgagcccctc acagaccgtc cagcgagcgg tgtctgtaaa tcccggtaaa | 11 |
| IgM ($C_H4$) | acgggcttct ctcccgcgga cgtcttcgtg cagtggatgc agagggggca gccctttgtcc ccggagaagt atgtgaccag cgccccaatg cctgagcccc aggccccagg ccggtacttc gcccacagca tcctgaccgt gtccgaagag gaatggaaca cgggggagac ctacacctgc gtggtggccc atgaggccct gcccaacagg gtcaccgaga ggaccgtgga caagtccacc ggtaaaccca ccctgtacaa cgtgtccctg gtcatgtccg acacacagctgg cacctgctac | 12 |
| IgG1 ($C_H3$) variant 1 | gtgtacaccc tgcccccatc ccgggatgag ctgaccaaga accaggtcag cctgacctgc ctggtcaaag gcttctatcc cagcgacatc gccgtggagt gggagagcaa tgggcagccg gagaacaact acaagaccac gcctcccgtg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccgggtaaa | 13 |
| IgG1 ($C_H3$) variant 2 | gggcagcccc gagaaccaca ggtgtacacc ctgcccccat ccgggatga gctgaccaag aaccaggtca gcctgacctg cctggtcaaa ggcttctatc cagcgacat cgccgtggag tgggagagca atgggcagcc ggagaacaac tacaagacca cacctcccgt gctggactcc gacggctcct tcttcctcta cagcaagctc accgtggaca agagcaggtg gcagcagggg aacgtcttct catgctccgt gatgcatgag gctctgcaca accactacac agaagagc ctctccctgt ctccgggtaa a | 28 |
| IgG2 ($C_H3$) variant 1 | gtgtacaccc tgcccccatc ccgggaggag atgaccaaga accaggtcag cctgacctgc ctggtcaaag gcttctaccc cagcgacatc gccgtggagt gggagagcaa tgggcagccg gagaacaact acaagaccac acctcccatg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccgggtaaa | 14 |
| IgG2 ($C_H3$) variant 2 | gggcagcccc gagaaccaca ggtgtacacc ctgcccccat cccgggagga gatgaccaag aaccaggtca gcctgacctg cctggtcaaa ggcttctacc cagcgacat ctccgtggag tgggagagca atgggcagcc ggagaacaac tacaagacca cacctcccat gctggactcc gacggctcct tcttcctcta cagcaagctc accgtggaca agagcaggtg gcagcagggg aacgtcttct catgctccgt gatgcatgag gctctgcaca accactacac gcagaagagc ctctccctgt ctccgggtaa a | 29 |
| IgG3 ($C_H3$) | gtgtacaccc tgcccccatc ccgggaggag atgaccaaga accaggtcag cctgacctgc ctggtcaaag gcttctaccc cagcgacatc gccgtggagt gggagagcag cgggcagccg gagaacaact acaacaccac gcctcccatg ctggactccg acggctcctt cttcctctac agcaagctca ccgtggacaa gagcaggtgg cagcagggga acatcttctc atgctccgtg atgcatgagg ctctgcacaa ccgcttcacg cagaagagcc tctccctgtc tccgggtaaa | 15 |
| IgG4 ($C_H3$) | gtgtacaccc tgcccccatc ccaggaggag atgaccaaga accaggtcag cctgacctgc ctggtcaaag gcttctaccc cagcgacatc gccgtggagt gggagagcaa tgggcagccg gagaacaact acaagaccac gcctcccgtg ctggactccg acggctcctt cttcctctac agcaggctaa ccgtggacaa gagcaggtgg caggaggga atgtcttctc atgctccgtg atgcatgagg ctctgcacaa ccactacaca cagaagagcc tctccctgtc tctgggtaaa | 16 |

In one embodiment the nucleic acid according to the invention encodes an amino acid sequence selected from the amino acid sequences of SEQ ID NO: 1, 3, 4, 5, 6, 7, or 8.

In one embodiment the nucleic acid encodes a part of the C-terminal constant domain of an immunoglobulin heavy chain of the class IgA, IgE, IgM, or IgG and is selected from the nucleic acids of SEQ ID NO: 17, 18, 19, 20, 21, 22, or 23, or 30, or 31. In another embodiment encodes the nucleic acid a part of the C-terminal constant domain of an immunoglobulin heavy chain of the class IgA, IgE, IgM, or IgG and is selected from the nucleic acids of SEQ ID NO: 17, 18, 19, 22, 23, 30, or 31. In a further embodiment encodes the nucleic acid a part of the C-terminal constant domain of an immunoglobulin heavy chain of the class IgA, IgE, IgM, or IgG and is selected from the nucleic acids of SEQ ID NO: 17, 18, 19, 22, or 23.

The nucleic acids with the nucleotide sequence of SEQ ID NO: 17 to 23 and 30 to 31 are also an aspect of the current invention. In one embodiment the nucleotide sequences of SEQ ID NO: 17, 18, 19, 22, 23, 30, or 31 are an aspect of the current invention. In another embodiment the nucleotide sequences of SEQ ID NO: 17, 18, 19, 22, or 23 are an aspect of the current invention.

In one embodiment encodes the nucleic acid the C-terminal constant domain of an immunoglobulin of the class IgA, IgE, IgM, or IgG, and comprises a nucleic acid selected from the nucleic acids of SEQ ID NO: 17, 18, 19, 20, 21, 22, or 23, or 30, or 31, which encodes a part of the C-terminal domain of the immunoglobulin heavy chain. In another embodiment encodes the nucleic acid the C-terminal constant domain of an immunoglobulin of the class IgA, IgE, IgM, or IgG, and comprises a nucleic acid selected from the nucleic acids of SEQ ID NO: 17, 18, 19, 22, 23, 30, or 31, which encodes a part of the C-terminal domain of the immunoglobulin heavy chain. In a further embodiment encodes the nucleic acid the C-terminal constant domain of an immunoglobulin of the class IgA, IgE, IgM, or IgG, and comprises a nucleic acid selected from the nucleic acids of SEQ ID NO: 17, 18, 19, 22, or 23, which encodes a part of the C-terminal domain of the immunoglobulin heavy chain.

TABLE 3

Nucleic acid sequences according to the invention encoding a part of the C-terminal constant domain amino acid sequence of an immunoglobulin heavy chain of different classes.

| immunoglobulin class | nucleic acid sequence encoding the C-terminal amino acid sequence | SEQ ID NO: |
|---|---|---|
| IgA | ggcaaaccca cccatgtcaa tgtgtctgtt gtcatggcgg aggtggacgg cacctgctac | 17 |
| IgE | catgaggcag cgagcccctc acagaccgtc cagcgagcgg tgtctgtaaa tcccggcaaa | 18 |
| IgM | ggcaaaccca ccctgtacaa cgtgtccctg gtcatgtccg acacagctgg cacctgctac | 19 |
| IgG1 variant 1 | atgcatgagg ctctgcacaa ccactacacg cagaagagcc tctccctgtc tccgggcaaa | 20 |
| IgG1 variant 2 | atgcatgagg ctctgcacaa ccactacaca cagaagagcc tctccctgtc tccgggcaaa | 30 |
| IgG2 variant 1 | atgcatgagg ctctgcacaa ccactacacg cagaagagcc tctccctgtc tccgggcaaa | 21 |
| IgG2 variant 2 | atctccgtgg agtgggagag caatgggcag ccggagaaca actacaagac cacacctccc atgctggact ccgacggctc cttcttcctc tacagcaagc tcaccgtgga caagagcagg tggcagcagg ggaacgtctt ctcatgctcc gtgatgcatg aggctctgca caaccactac acgcagaaga gcctctccct gtctccgggc aaa | 31 |
| IgG3 | atgcatgagg ctctgcacaa ccgcttcacg cagaagagcc tctccctgtc tccgggcaaa | 22 |
| IgG4 | atgcatgagg ctctgcacaa ccactacaca cagaagagcc tctccctgtc tctgggcaaa | 23 |

The nucleic acid according to the invention encodes at least a part of the C-terminal constant domain of an immunoglobulin of the class IgA, IgE, IgM, or IgG. The term "C-terminal constant domain" denotes either the $C_H3$-domain of an immunoglobulin heavy chain of the class IgA or IgG, or the $C_H4$-domain of an immunoglobulin heavy chain of the class IgE or IgM. The expression "a part of" denotes a C-terminal fraction of the C-terminal constant domain of an immunoglobulin heavy chain of the class IgA, IgE, IgM, or IgG, of at least 20 consecutive amino acids, or of at least 50 consecutive amino acids, or of at least 100 consecutive amino acids of the primary amino acid sequence counted from the C-terminus in direction to the N-terminus of the immunoglobulin heavy chain.

Recombinant production of immunoglobulins is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160 Werner, R. G., Arzneimittelforschung—Drug Research 48 (1998) 870-880.

For the production of an immunoglobulin comprising an amino acid sequence encoded by a nucleic acid according to the invention the invention further comprises a method for the production of an immunoglobulin in a mammalian cell comprising the following steps:

a) transfecting the mammalian cell with a nucleic acid encoding an immunoglobulin heavy chain, wherein a nucleic acid selected from the nucleic acids of SEQ ID NO: 17, 18, 19, 20, 21, 22, or 23, or 30, or 31 encodes a part of the C-terminal domain of the immunoglobulin heavy chain, b) cultivating the transfected mammalian cell under conditions suitable for the expression of the immunoglobulin, c) recovering the immunoglobulin from the culture or the cell.

The term "under conditions suitable for the expression of the immunoglobulin" denotes conditions, which are used for the cultivation of a mammalian cell expressing an immunoglobulin and which are known to or can easily be determined by a person skilled in the art. It is also known to a person skilled in the art that these conditions may vary depending on the type of mammalian cell cultivated and type of immunoglobulin expressed. In general the mammalian cell is cultivated at a temperature, e.g. between 20° C. and 40° C., and for a period of time sufficient to allow effective protein production of the immunoglobulin, e.g. for 4 to 28 days.

In one embodiment the transfecting the mammalian cell is with a nucleic acid encoding an immunoglobulin heavy chain, wherein a nucleic acid selected from the nucleic acids of SEQ ID NO: 17, 18, 19, 22, 23, 30, or 31 encodes a part of the C-terminal domain of the immunoglobulin heavy chain. In a further embodiment the transfecting the mammalian cell is with a nucleic acid encoding an immunoglobulin heavy chain, wherein a nucleic acid selected from the nucleic acids of SEQ ID NO: 17, 18, 19, 22, or 23 encodes a part of the C-terminal domain of the immunoglobulin heavy chain. In one embodiment the mammalian cell is transfected with a, i.e. one, nucleic acid comprising an expression cassette encoding an immunoglobulin heavy chain and an expression cassette encoding an immunoglobulin light chain. In another embodiment is the mammalian cell transfected with two nucleic acids, one comprising an expression cassette encoding an immunoglobulin light chain, and one comprising an expression cassette encoding an immunoglobulin heavy chain.

The immunoglobulin produced with the method according to the invention is preferably a heterologous immunoglobulin. The term "heterologous immunoglobulin" denotes an immunoglobulin which is not naturally produced by said mammalian cell. The immunoglobulin produced according to the method of the invention is produced by recombinant means. Such methods are widely known in the state of the art and comprise protein expression in prokaryotic and eukaryotic cells with subsequent recovery and isolation of the heterologous immunoglobulin, and usually purification to a pharmaceutically acceptable purity. For the production, i.e. expression, of an immunoglobulin a nucleic acid encoding the light chain and a nucleic acid encoding the heavy chain, which is comprising the nucleic acid according to the invention, are inserted each into an expression cassette by standard methods. Nucleic acids encoding immunoglobulins are readily isolated and sequenced using conventional procedures. Hybridoma cells can serve as a source of such nucleic acids. The expression cassettes may be inserted into an expression plasmid(s), which is (are) then transfected into host cells, which do not otherwise produce immunoglobulins. Expression is performed in appropriate prokaryotic or eukaryotic host cells and the immunoglobulin is recovered from the cells after lysis or from the culture supernatant.

Different methods are well established and widespread used for protein recovery and purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A. Appl. Biochem. Biotech. 75 (1998) 93-102).

The current invention further comprises a nucleic acid encoding an immunoglobulin heavy chain comprising the nucleic acid according to the invention. Furthermore comprises the invention a plasmid comprising the nucleic acid according to the invention and a cell comprising this plasmid.

Another aspect of the current invention is a method for improving the expression of an immunoglobulin in a mammalian cell, wherein the nucleic acid encoding the immunoglobulin heavy chain comprises the nucleic acid ggaaaa, or the nucleic acid ggcaaa, or the nucleic acid gggaaa, or the nucleic acid ggaaag, or the nucleic acid ggcaag, or the nucleic acid gggaag, encoding the glycine-lysine-dipeptide contained in the $C_H3$- or $C_H4$-domain. With this nucleic acid unwanted splicing events can be reduced or suppressed.

In one embodiment of the invention the immunoglobulin heavy chain is either an immunoglobulin heavy chain of a human antibody of the subclass IgG4 or an immunoglobulin heavy chain of a human antibody of the subclass IgG1, IgG2, or IgG3. In one embodiment the immunoglobulin heavy chain is a human immunoglobulin heavy chain and preferably either from human IgG4 subclass or a mutated immunoglobulin heavy chain from human IgG1 subclass. In another embodiment the immunoglobulin heavy chain is from human IgG1 subclass with mutations L234A and L235A. In a further embodiment the immunoglobulin heavy chain is a human IgG4 immunoglobulin heavy chain with the mutation S228P. In on embodiment the immunoglobulin heavy chain is of IgG4 subclass or of IgG1 or IgG2 subclass, with a mutation in L234, L235, and/or D265, and/or contains the PVA236 mutation. In other embodiments the mutations are S228P, L234A, L235A, L235E, and/or PVA236 (PVA236 means that the amino acid sequence ELLG (given in one letter amino acid code) from amino acid position 233 to 236 of IgG1 or EFLG of IgG4 is replaced by PVA). Preferred are the mutations S228P of IgG4, and L234A and L235A of IgG1 (numbering according to EU index of Kabat).

"Regulatory elements" as used herein, refer to nucleotide sequences present in cis, necessary for transcription and/or translation of the nucleic acid sequence encoding a polypeptide of interest. The transcriptional regulatory elements normally comprise a promoter upstream of the nucleic acid sequence to be expressed, transcriptional initiation and termination sites, and a polyadenylation signal sequence. The term "transcriptional initiation site" refers to the nucleic acid base in the nucleic acid corresponding to the first nucleic acid incorporated into the primary transcript, i.e. the mRNA precursor; the transcriptional initiation site may overlap with the promoter sequence. The term "transcriptional termination site" refers to a nucleotide sequence normally represented at the 3' end of a gene of interest to be transcribed, that causes RNA polymerase to terminate transcription. The polyadenylation signal sequence, or poly-A addition signal provides the signal for the cleavage at a specific site at the 3' end of eukaryotic mRNA and the post-transcriptional addition in the nucleus of a sequence of about 100-200 adenine nucleotides (polyA tail) to the cleaved 3' end. The polyadenylation signal sequence may include the consensus sequence AATAAA located at about 10-30 nucleotides upstream from the site of cleavage.

To produce a secreted polypeptide, the nucleic acid of interest includes a DNA segment that encodes a signal sequence/leader peptide. The signal sequence directs the newly synthesized polypeptide to and through the ER membrane where the polypeptide can be routed for secretion. The signal sequence is cleaved off by a signal peptidases during the protein crosses the ER membrane. As for the function of the signal sequence the recognition by the host cell's secretion machinery is essential. Therefore the used signal sequence has to be recognized by the host cell's proteins and enzymes of the secretion machinery.

Translational regulatory elements include a translational initiation (AUG) and stop codon (TAA, TAG or TGA). An internal ribosome entry site (IRES) can be included in some constructs.

A "promoter" refers to a polynucleotide sequence that controls transcription of a gene/structural gene or nucleic acid sequence to which it is operably linked. A promoter includes signals for RNA polymerase binding and transcription initiation. The promoters used will be functional in the cell type of the host cell in which expression of the selected sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). A "promoter" comprises a nucleotide sequence that directs the transcription of a structural gene. Typically, a promoter is located in the 5' non-coding or untranslated region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee, R. E., et al., Mol. Endocrinol. 7 (1993) 551-560), cyclic AMP response elements (CREs), serum response elements (SREs; Treisman, R., Seminars in Cancer Biol. 1 (1990) 47-58), glucocorticoid response elements (GREs), and binding sites for other transcription factors, such as CRE/ATF (Treisman, R., Seminars in Cancer Biol. 1 (1990) 47-58; O'Reilly, M. A., et al., J. Biol. Chem. 267 (1992) 19938), AP2 (Ye, J., et al., J. Biol. Chem. 269 (1994) 25728), SP1, cAMP response element binding protein (CREB; Loeken, M. R., Gene Expr. 3 (1993) 253) and octamer factors (see, in general, Watson et al., eds., Molecular Biology of the Gene, 4th ed. (The Benjamin/Cummings Publishing Company, Inc. 1987), and Lemaigre, F. P. and Rousseau, G. G., Biochem. J. 303 (1994) 1-14). If a promoter is an inducible promoter, then the rate of transcription increases in response to an inducing agent. In contrast, the rate of transcription is not regulated by an inducing agent if the promoter is a constitutive promoter. Repressible promoters are also known. For example, the c-fos promoter is specifically activated upon binding of growth hormone to its receptor on the cell surface. Tetracycline (tet) regulated expression can be achieved by artificial hybrid promoters that consist e.g. of a CMV promoter followed by two Tet-operator sites. The Tet-repressor binds to the two Tet-operator sites and blocks transcription. Upon addition of the inducer tetracycline, Tet-repressor is released from the Tet-operator sites and transcription proceeds (Gossen, M. and Bujard, H. PNAS 89 (1992) 5547-5551). For other inducible promoters including metallothionein and heat shock promoters, see, e.g., Sambrook et al. (supra) and Gossen, M., Curr. Opin. Biotech. 5 (1994) 516-520. Among the eukaryotic promoters that have been identified as strong promoters for high-level expression are the SV40 early promoter, adenovirus major late promoter, mouse metallothionein-I promoter, Rous sarcoma virus long terminal repeat, Chinese hamster elongation factor 1 alpha (CHEF-1, see e.g. U.S. Pat. No. 5,888,809), human EF-1 alpha, ubiquitin, and human cytomegalovirus immediate early promoter (CMV IE).

The "promoter" can be constitutive or inducible. An enhancer (i.e., a cis-acting DNA element that acts on a promoter to increase transcription) may be necessary to function in conjunction with the promoter to increase the level of expression obtained with a promoter alone, and may be included as a transcriptional regulatory element. Often, the polynucleotide segment containing the promoter will include enhancer sequences as well (e.g., CMV or SV40).

An "enhancer", as used herein, refers to a polynucleotide sequence that enhances transcription of a gene or coding sequence to which it is operably linked. Unlike promoters, enhancers are relatively orientation and position independent and have been found 5' or 3' (Lusky, M., et al., Mol. Cell Bio., 3 (1983) 1108-1122) to the transcription unit, within an intron (Banerji, J., et al., Cell, 33 (1983) 729-740) as well as within the coding sequence itself (Osborne, T. F., et al., Mol. Cell Bio., 4 (1984) 1293-1305). Therefore, enhancers may be placed upstream or downstream from the transcription initiation site or at considerable distances from the promoter, although in practice enhancers may overlap physically and functionally with promoters. A large number of enhancers, from a variety of different sources are well known in the art (and identified in databases such as GenBank) and available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences. For example, all of the strong promoters listed above may also contain strong enhancers (see e.g. Bendig, M. M., Genetic Engineering, 7 (Academic Press, 1988) 91-127).

An "internal ribosome entry site" or "IRES" describes a sequence which functionally promotes translation initiation independent from the gene 5' of the IRES and allows two cistrons (open reading frames) to be translated from a single transcript in an animal cell. The IRES provides an independent ribosome entry site for translation of the open reading frame immediately downstream (downstream is used interchangeably herein with 3') of it. Unlike bacterial mRNA which can be polycistronic, i.e. encode several different polypeptides that are translated sequentially from the mRNAs, most mRNAs of animal cells are monocistronic and code for the synthesis of only one protein. With a monocistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an IRES operably linked to the second or subsequent open reading frame in the transcript allows the sequential translation of that downstream open reading frame to produce the two or more polypeptides encoded by the same transcript. The use of IRES elements in vector construction has been previously described, see, e.g., Pelletier, J., et al., Nature 334 (1988) 320-325; Jang, S. K., et al., J. Virol. 63 (1989) 1651-1660; Davies, M. V., et al., J. Virol. 66 (1992) 1924-1932; Adam, M. A., et al. J. Virol. 65 (1991) 4985-4990; Morgan, R. A., et al. Nucl. Acids Res. 20 (1992) 1293-1299; Sugimoto, Y, et al. Biotechnology 12 (1994) 694-698; Ramesh, N., et al. Nucl. Acids Res. 24 (1996) 2697-2700; and Mosser, D. D. et al, BioTechniques 22 (1997) 150-161).

"Operably linked" refers to a juxtaposition of two or more components, wherein the components so described are in a relationship permitting them to function in their intended manner. For example, a promoter and/or enhancer are operably linked to a coding sequence, if it acts in cis to control or modulate the transcription of the linked sequence. Generally, but not necessarily, the DNA sequences that are "operably linked" are contiguous and, where necessary to join two protein encoding regions such as a secretory leader and a polypeptide, contiguous and in (reading) frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence if it is located at the downstream end of the coding sequence such that transcription proceeds through the coding sequence into the polyadenylation sequence. A translation stop codon is operably linked to an exonic nucleic acid sequence if it is located at the downstream end (3' end) of the coding sequence such that translation proceeds through the coding sequence to the stop codon and is terminated there. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

"Heterologous DNA" or "heterologous polypeptide" refers to a DNA molecule or a polypeptide, or a population of DNA molecules or a population of polypeptides, that do not exist naturally within a given host cell. DNA molecules heterologous to a particular host cell may contain DNA derived from the host cell species (i.e. endogenous DNA) so long as that host DNA is combined with non-host DNA (i.e. exogenous DNA). For example, a DNA molecule containing a non-host DNA segment encoding a polypeptide operably linked to a host DNA segment comprising a promoter is considered to be a heterologous DNA molecule. Conversely, a heterologous DNA molecule can comprise an endogenous structural gene operably linked with an exogenous promoter.

A peptide or polypeptide encoded by a non-host DNA molecule is a "heterologous" peptide or polypeptide.

An "expression plasmid" is a nucleic acid molecule encoding a protein to be expressed in a host cell. Typically, an expression plasmid comprises a prokaryotic plasmid propagation unit, e.g. for E. coli, comprising an origin of replication, and a selection marker, an eukaryotic selection marker, and one or more expression cassettes for the expression of the structural gene(s) of interest each comprising a promoter, a structural gene, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e. at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

"Transcription terminator" as denoted within this application is a DNA sequence of 50-750 base pairs in length which gives the RNA polymerase the signal for termination of the mRNA synthesis. Very efficient (strong) terminators at the 3' end of an expression cassette are advisable to prevent the RNA polymerase from reading through particularly when using strong promoters. Inefficient transcription terminators can lead to the formation of an operon-like mRNA which can be the reason for an undesired, e.g. plasmid-coded, gene expression.

The following examples, sequence listing and figures are provided to aid the understanding of the present invention, the true scope of which is set forth in the appended claims. It is understood that modifications can be made in the procedures set forth without departing from the spirit of the invention.

Description Of The Sequences

SEQ ID NO: 01 C-terminal part of the heavy chain constant domain ($C_H3$) amino acid sequence of a human IgA class immunoglobulin SEQ ID NO: 02 C-terminal part of the heavy chain constant domain ($C_H3$) amino acid sequence of a human IgD class immunoglobulin SEQ ID NO: 03 C-terminal part of the heavy chain constant domain ($C_H4$) amino acid sequence of a human IgE class immunoglobulin SEQ ID NO: 04 C-terminal part of the heavy chain constant domain ($C_H4$) amino acid sequence of human IgM class immunoglobulin SEQ ID NO: 05 C-terminal part of the heavy chain constant domain ($C_H3$) amino acid sequence of a human IgG1 class immunoglobulin SEQ ID NO: 06 C-terminal part of the heavy chain constant domain ($C_H3$) amino acid sequence of a human IgG2 class immunoglobulin SEQ ID NO: 07 C-terminal part of the heavy chain constant domain ($C_H3$) amino acid sequence of a human IgG3 class immunoglobulin SEQ ID NO: 08 C-terminal part of the heavy chain constant domain ($C_H3$) amino acid sequence of a human IgG4 class immunoglobulin SEQ ID NO: 09 Nucleic acid sequence encoding the C-terminal part of the heavy chain constant domain ($C_H3$) amino acid sequence of a human IgA class immunoglobulin SEQ ID NO: 10 Nucleic acid sequence encoding the C-terminal part of the heavy chain constant domain ($C_H3$) amino acid sequence of a human IgD class immunoglobulin SEQ ID NO: 11 Nucleic acid sequence encoding the C-terminal part of the heavy chain constant domain ($C_H4$) amino acid sequence of a human IgE class immunoglobulin SEQ ID NO: 12 Nucleic acid sequence encoding the C-terminal part of the heavy chain constant domain ($C_H4$) amino acid sequence of a human IgM class immunoglobulin SEQ ID NO: 13, 28 Nucleic acid sequence encoding the C-terminal part of the heavy chain constant domain ($C_H3$) amino acid sequence of a human IgG1 class immunoglobulin (variant 1 and 2)

SEQ ID NO: 14, 29 Nucleic acid sequence encoding the C-terminal part of the heavy chain constant domain ($C_H3$) amino acid sequence of a human IgG2 class immunoglobulin (variant 1 and 2)

SEQ ID NO: 15 Nucleic acid sequence encoding the C-terminal part of the heavy chain constant domain ($C_H3$) amino acid sequence of a human IgG3 class immunoglobulin SEQ ID NO: 16 Nucleic acid sequence encoding the C-terminal part of the heavy chain constant domain ($C_H3$) amino acid sequence of a human IgG4 class immunoglobulin SEQ ID NO: 17 Nucleic acid sequence according to the invention encoding a part of the C-terminal constant domain ($C_H3$) amino acid sequences of an IgA class immunoglobulin SEQ ID NO: 18 Nucleic acid sequence according to the invention encoding a part of the C-terminal constant domain ($C_H4$) amino acid sequences of an IgE class immunoglobulin SEQ ID NO: 19 Nucleic acid sequence according to the invention encoding a part of the C-terminal constant domain ($C_H4$) amino acid sequences of an IgM class immunoglobulin SEQ ID NO: 20, 30 Nucleic acid sequence according to the invention encoding a part of the C-terminal constant domain ($C_H3$) amino acid sequences of an IgG1 class immunoglobulin (variant 1 and 2)

SEQ ID NO: 21, 31 Nucleic acid sequence according to the invention encoding a part of the C-terminal constant domain ($C_H3$) amino acid sequences of an IgG2 class immunoglobulin (variant 1 and 2)

SEQ ID NO: 22 Nucleic acid sequence according to the invention encoding a part of the C-terminal constant domain ($C_H3$) amino acid sequences of an IgG3 class immunoglobulin SEQ ID NO: 23 Nucleic acid sequence according to the invention encoding a part of the C-terminal constant domain ($C_H3$) amino acid sequences of an IgG4 class immunoglobulin SEQ ID NO: 24 to 27 Nucleic acid primers used in the Examples.

MATERIALS AND METHODS

Recombinant DNA Techniques

Figure 1:
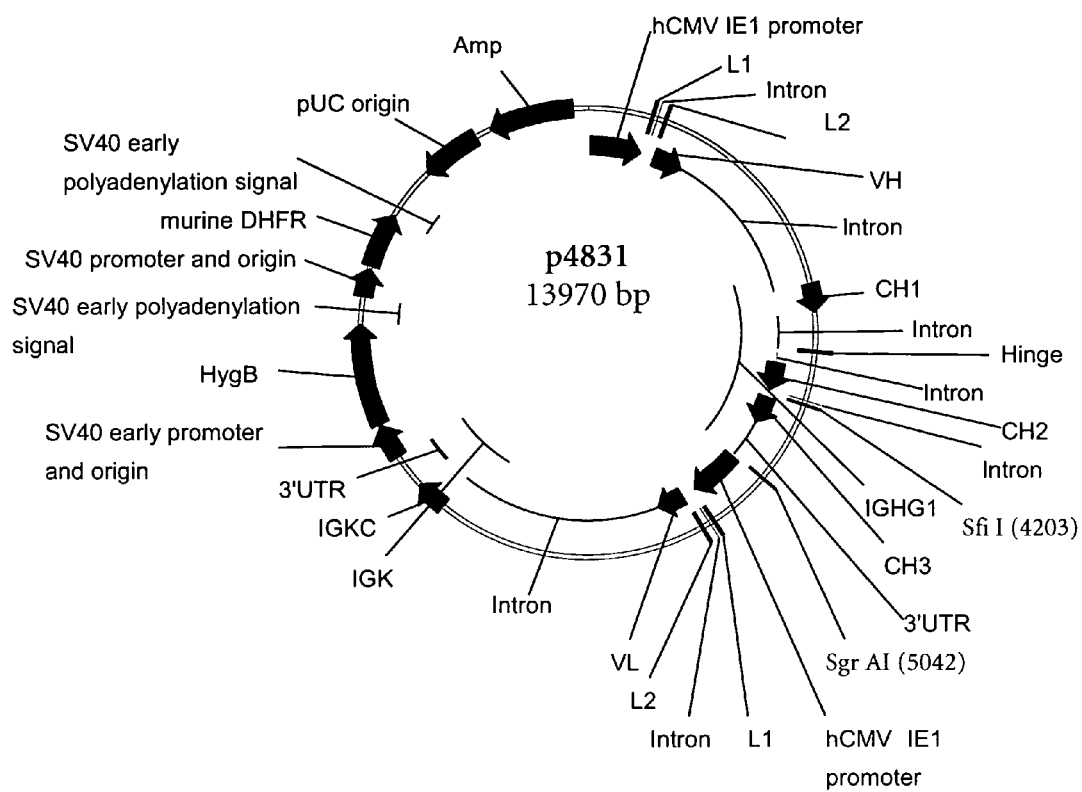
FIG. 1 Annotated plasmid map of p4831.

Standard methods were used to manipulate DNA as described in Sambrook et al., 1989 (supra). All molecular biological reagents were commercially available (if not indicated otherwise) and were used according to the manufacturer's instructions.

Nucleic Acid Sequence Determination

DNA sequences were determined by double strand sequencing performed at MediGenomix GmbH (Martinsried, Germany).

DNA and Protein Sequence Analysis and Sequence Data Management

The GCG's (Genetics Computer Group, Madison, Wis., USA) software package version 10.2 and Infomax's Vector NTI Advance suite version 8.0 was used for sequence creation, mapping, analysis, annotation, and illustration.

Cell Culture Techniques

CHO-DXB11 cells were grown in MEM alpha medium (Invitrogen Corp., Gibco®, Cat. No.: 22571) with 10% FCS (fetal calf serum obtained from Hyclone, Thermo Fisher Scientific Inc., Cat. No.: SH3007.03).

HEK-293-EBNA cells (ATCC #CRL-10852) were cultivated in DMEM, supplemented with 2 mM glutamine (Gibco®, Cat. No.: 25030), 1% (v/v) MEM non essential amino acids (Gibco®, Cat. No.: 11140), 10% (v/v) ultra-low IgG FCS (Gibco®, Cat. No.: 16250), and 250 µg/ml G418 (Roche Applied Sciences, Roche Diagnostics GmbH, Germany, Cat. No.: 1464981).

The medium for the cultivation of CHO-DG44 cells was MEM alpha medium (Gibco®, Cat. No.: 22561) supplemented with 10% (v/v) dialyzed FCS (Gibco®, Cat. No.: 26400) and 2% (v/v) HT supplement (Gibco®, Cat. No.: 41065). For the selection of stably transfected CHO DG44 cell lines the HT supplement was omitted and 20 to 500 nM Methotrexate (MTX) was added either alone or in combination with 400 µg/ml Hygromycin B (Roche Diagnostics GmbH, Roche Applied Sciences, Germany, Cat. No.: 10843555001).

All cell lines were maintained in humidified incubators at 37° C. with 5% $CO_2$. Transfection of cells was either performed by nucleofection (Amaxa GmbH, Germany) or by lipofection using FuGENE 6 (Roche Diagnostics GmbH, Roche Applied Sciences, Germany, Cat. No.: 1815075).

Furthermore standard cell culture techniques were applied as described e.g. in Bonifacino, J. S., et al. (Eds) (2000) Current Protocols in Cell Biology, John Wiley and Sons, Inc.

Protein A-Precipitation, SDS-PAGE and Western Blot

Immunoglobulins from cell culture supernatants were precipitated with Protein A-Sepharose beads and then analyzed by SDS/polyacrylamide gel electrophoresis (sodium dodecyl sulfate, SDS-PAGE) and Western-blotting.

For precipitation of immunoglobulins cell culture supernatants containing up to 7 µg immunoglobulin were diluted with TBS buffer (50 mM TRIS/HCl, pH 7.5, supplemented with 150 mM NaCl), 1% (v/v) Nonidet-P40 (Roche Diagnostics GmbH, Roche Applied Sciences, Cat. No.: 1754599) to a final volume of 1 ml, and afterwards incubated for one hour with 15 µl wet volume Protein A-Sepharose beads. The beads were recovered by centrifugation and washed with TBS with 1% (v/v) Nonidet P-40, thereafter with 2-fold concentrated PBS (phosphate buffered saline), and finally with 100 mM sodium citrate buffer, pH 5. After the final wash step the supernatant was removed completely from the beads. Bound immunoglobulins were eluted with 20 µl 2-fold concentrated LDS (lithium dodecyl sulfate) sample buffer (Invitrogen Corp.) containing 50 mM DTT (dithiothreitol). After 5 minutes incubation at 95° C. the suspension was centrifuged and the supernatant was recovered for further analysis.

SDS-PAGE: SDS-PAGE was performed using the NuPAGE® gel system (Invitrogen Corp.) according to the manufacturer's recommendations. Samples were loaded onto 10% NuPAGE® Novex Bis/TRIS gels (Invitrogen Corp., Cat. No.: NP0301) and proteins were separated in reducing NuPAGE® MES SDS (4-morpholinoethanesulfonic acid/sodium dodecyl sulfate) running buffer. Typically 2 to 3 µg immunoglobulin per lane was loaded for Coomassie staining with Simply Blue Safe Stain® (Invitrogen Corp.) and 0.4 to 0.6 µg for Western-blotting.

Western Blot: For electro-transfer of proteins from SDS/polyacrylamide gels standard PVDF (polyvinylidene difluoride) or nitrocellulose membranes were used. After electro-transfer membranes were washed in TBS (tries buffered saline, 50 mM TRIS/HCl, pH 7.5, 150 mM NaCl). Nonspecific binding sites were blocked by incubation in TBS with 1% (w/v) Western Blocking Reagent (Roche Diagnostics GmbH, Roche Applied Sciences, Cat. No.: 11921673001). Human immunoglobulin gamma heavy chains and kappa light chains were detected with peroxidase coupled polyclonal detection antibodies (see following paragraph for further details) diluted in TBS with 0.5% (w/v) Western Blocking Reagent. After three wash steps with TBS with 0.05% (v/v) Tween® 20, and one wash step with TBS, bound peroxidase coupled detection antibodies were detected by chemoluminescence using LumiLightPlus substrate solution (Roche Diagnostics GmbH, Roche Applied Sciences, Cat. No.: 12015196001) and LUMI-Imager F1 analyzer (Roche Diagnostics GmbH, Roche Applied Sciences).

Human immunoglobulin gamma heavy chains (H) and kappa light chains (L) were detected either simultaneously or separately. For simultaneous detection peroxidase coupled goat anti-human IgG (H+L)-antibody (Jackson ImmunoResearch Laboratories Inc., Cat. No.: 109-035-088) was used at a dilution of 1:2500 (v/v). For consecutive detection, membranes were first probed with peroxidase coupled rabbit anti-human Ig gamma-antibody (DAKO GmbH, Germany, code no. P0214) at a dilution of 1:1000 (v/v) or with peroxidase coupled F(ab')$_2$ goat anti-human Fc gamma-antibody (Jackson ImmunoResearch Laboratories, Cat. No.: 109-036-008) at a dilution of 1:7500 (v/v). After detection of the immunoglobulin gamma heavy chain, the membranes were stripped for 30 minutes in 62.5 mM TRIS/HCl, pH 6.7, supplemented with 2% (w/v) SDS and 100 mM β-mercaptoethanol, at 50° C. For the second detection the membranes were re-probed with peroxidase coupled rabbit anti-human Ig kappa-antibody (DAKO GmbH, code no. P0129) at a dilution of 1:1000 (v/v).

EXAMPLE 1

Preparation of an Expression Plasmid for an Immunoglobulin of Class IgG1

Plasmid 4831 (denoted as p4831 in the following) is the expression plasmid for the expression of an anti-IGF-1R-antibody (genomically organized expression cassette with retained exon-intron organization) in eukaryotic cells (for sequences see e.g. US 2005/0008642, or EP 1 646 720). It comprises the following functional elements:
an origin of replication derived from the vector pUC18 (pUC origin),
a β(beta)-lactamase gene conferring ampicillin resistance in *E. coli* (Amp),
an expression cassette for the expression of a gamma 1-heavy chain comprising the following elements
the major immediate-early promoter and enhancer from the human cytomegalovirus (hCMV IE1 promoter),
a synthetic 5'UTR including a Kozak sequence,
a murine immunoglobulin heavy chain signal sequence including the signal sequence intron (L1_Intron_L2),
the cDNA for a heavy chain variable region (VH) arranged with a splice donor site at the 3' end,
the mouse immunoglobulin μ-enhancer region,
a human immunoglobulin heavy chain gamma 1-gene (IGHG1) including exons CH1, Hinge, CH2 and CH3, intervening introns and the 3'UTR bearing the polyadenylation signal sequence and optionally containing mutations,
an expression cassette for the expression of a kappa-light chain comprising the following elements
the major immediate-early promoter and enhancer from the human cytomegalovirus (hCMV IE1 promoter),
a synthetic 5'UTR including a Kozak sequence,
a murine immunoglobulin heavy chain signal sequence including the signal sequence intron (L1_Intron_L2),
the cDNA for a light chain variable region arranged with a splice donor site at the 3' end (VL),
the intronic mouse Ig-kappa enhancer region,
the human immunoglobulin kappa gene (IGK) including the IGKC exon and the IGK 3'UTR bearing the polyadenylation signal sequence.
a Hygromycin B phosphotransferase transcription unit suitable for selection in eukaryotic cells including
the SV40 early promoter and origin,
the hygromycin B phosphotransferase coding sequence (HygB),
the SV40 early polyadenylation signal
an expression cassette for the expression of murine dihydrofolate reductase (DHFR) suitable for auxotrophic selection in eukaryotic cells including
a shortened version of the SV40 early promoter and origin,
the coding sequence for murine DHFR,
the SV40 early polyadenylation signal.
An annotated plasmid map of p4831 is shown in FIG. 1.

Figure 2:
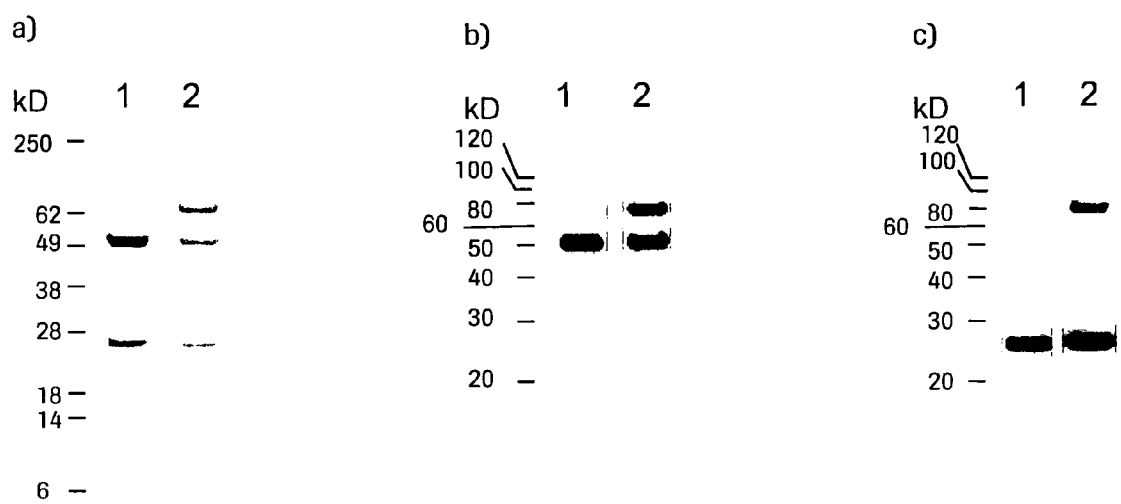
FIG. 2 SDS-PAGE and Western blot analysis of antibodies secreted by clone #23; a) Coomassie staining, b) Western blot analysis with peroxidase coupled anti-human immunoglobulin gammy chain-antibody, c) Western blot analysis with peroxidase coupled anti-human immunoglobulin kappa light chain-antibody. Lane 1: human anti-IGF-1R-reference antibody; lane 2: culture supernatant of CHO-DG44 clone #23 comprising the antibody of clone #23.

P4831 was transfected into CHO-DG44 cells and stable cell lines were isolated after selection with Hygromycin B and Methotrexate (MTX). Antibodies secreted by selected clone #23 were precipitated with Protein A-Sepharose beads and analyzed by SDS-PAGE and Coomassie staining (FIG. 2a)). In addition to the expected 50 kDa immunoglobulin gamma-1 heavy chain and the 25 kDa immunoglobulin kappa light chain, considerable amounts of an 80 kDa by-product protein were detected. This protein was recognized by anti-human immunoglobulin gamma chain antibodies (FIG. 2b)) as well as by anti-human immunoglobulin kappa chain antibodies (FIG. 2c)).

EXAMPLE 2

Preparation of an Expression Plasmid for an Immunoglobulin of Class IgG1 with a Modified CH3-Domain In order to prevent the generation of by-products resulting from aberrantly spliced gamma 1 pre-mRNA, the internal splice site of the CH3 exon of p4831 was destroyed by mutating the T in position 4573 to C. At the same time T4567 was replaced by C for removal of a BsmA I restriction site.

Figure 3:
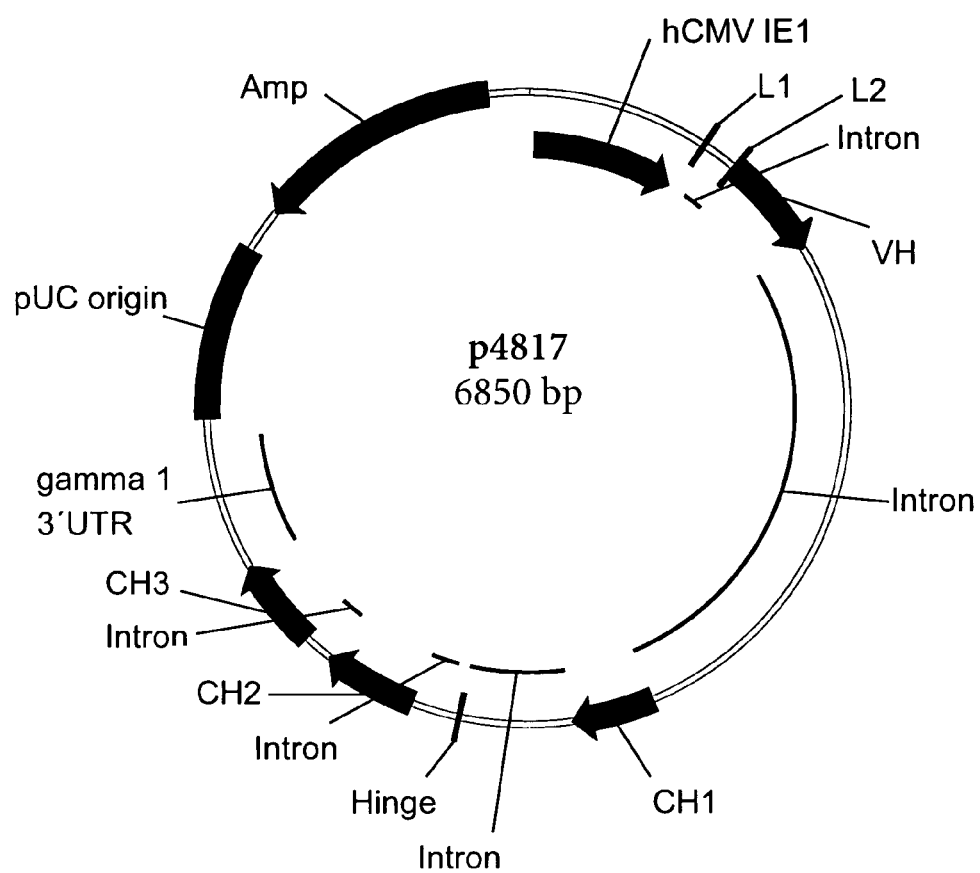
FIG. 3 Annotated plasmid map of p4817.

P4855 was constructed as follows. p4817, an ancestor plasmid of p4831 with the same gamma 1 heavy chain transcription unit, is composed of the following elements:
an origin of replication from the vector pUC18 which allows replication of this plasmid in *E. coli* (pUC Ori)
a beta-lactamase gene which confers ampicillin resistance in *E. coli* (Amp)
an expression cassette for the expression of a gamma1-heavy chain comprising the following elements
the major immediate-early promoter and enhancer from the human cytomegalovirus (hCMV IE1 promoter),
a synthetic 5'UTR including a Kozak sequence,
a murine immunoglobulin heavy chain signal sequence including the signal sequence intron (L1_Intron_L2),
the cDNA for a heavy chain variable region (VH) arranged with a splice donor site at the 3' end,
the mouse immunoglobulin μ-enhancer region,
a human immunoglobulin heavy chain gamma 1-gene (IGHG1) including exons CH1, Hinge, CH2 and CH3, intervening introns and the 3'UTR bearing the polyadenylation signal sequence and optionally containing mutations,
The plasmid map of p4817 is shown in FIG. 3.

P4817 was manipulated by site-directed mutagenesis using the QuickChange Site-Directed Mutagenesis Kit (Stratagene, Cat. No.: 200518) and the sequence specific oligonucleotides 1

```
                                     SEQ ID NO: 24
      agcctctccc tgtccccggg caaatgagtg cgacggccg
``` and 2

```
                                     SEQ ID NO: 25
     cggccgtcgc actcatttgc ccggggacag ggagaggct.
```

The 839 by SfiI/SgrAI fragment of mutated p4817 was excised and ligated with the 13133 by SgrAI/SfiI fragment of p4831 to form p4855.

EXAMPLE 3

Figure 4:
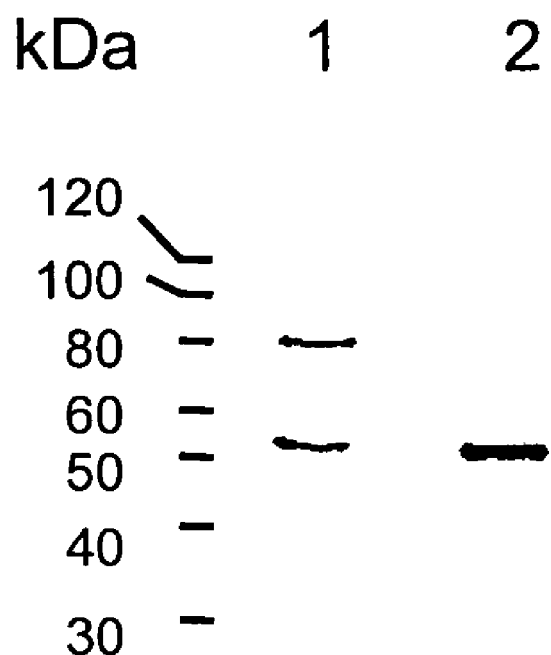
FIG. 4 Western blot analyses of immunoglobulins secreted by CHO-DXB11 transfected with p4831 or 4855. Lane 1: CHO cells transfected with p4831, lane 2: CHO cells transfected with p4855.

Expression of Nucleic Acids According to Example 1 and 2, Isolation of the Produced Immunoglobulin, and Analysis of the Produced Immunoglobulin Plasmids p4831 and p4855 were transiently transfected into CHO-DXB11 cells. The cells were cultivated under non-selective conditions. After three days of cultivation the cell culture supernatants were harvested and the secreted immunoglobulins were purified with Protein A-Sepharose beads. Western blot analysis of the immunoglobulins with anti-human IgG-antibodies (H+L) showed that the 80 kDa by-product had been expressed by the cells transfected with p4831 but not by the cells transfected with p4855 (FIG. 4).

EXAMPLE 4

Preparation of an Expression Plasmid for an Immunoglobulin of Class IgG4

Figure 5:
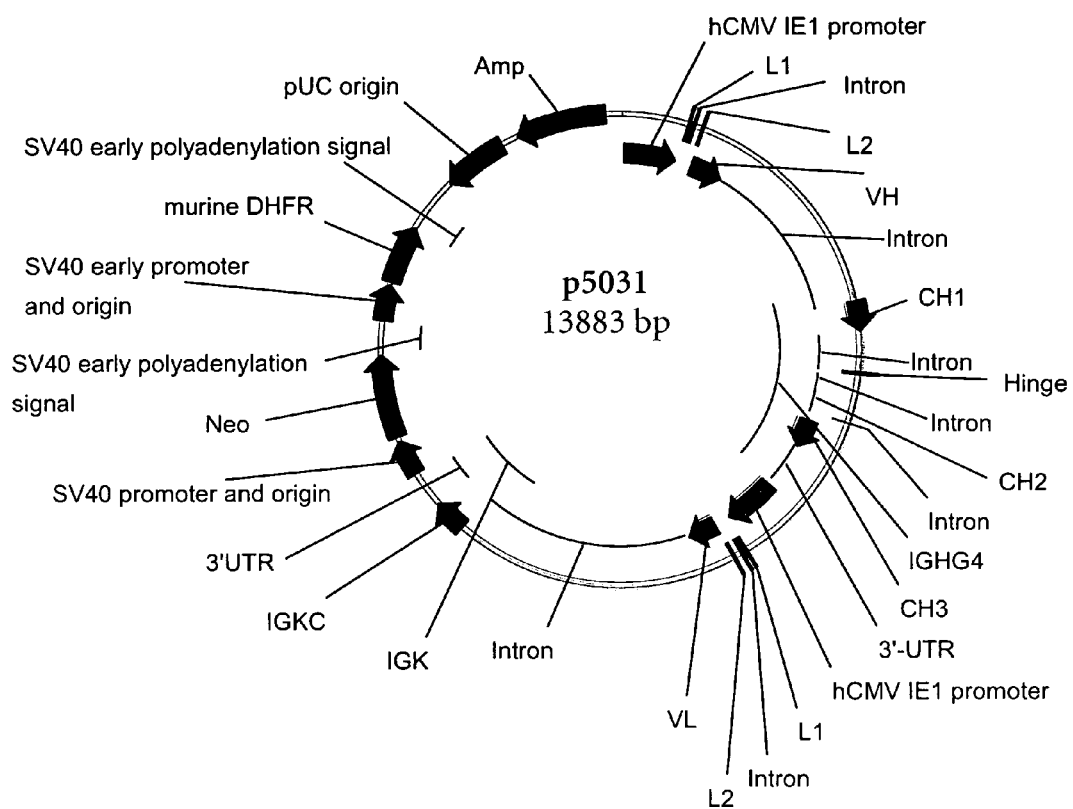
FIG. 5 Annotated plasmid map of p5031.

Plasmid 5031 was designed for transient and stable expression of a human anti-P-selectin-antibody in eukaryotic tissue culture cell. For exemplary anti-P-selectin-antibodies see e.g. EP 1 737 891 or US 2005/0226876. P5031 is composed of the following elements
an origin of replication from the vector pUC18 which allows replication of this plasmid in *E. coli* (pUC origin),
a β-lactamase gene which confers ampicillin resistance in *E. coli* (Amp),
an expression cassette for the expression of a human gamma 4-heavy chain comprising the following elements:
the major immediate-early promoter and enhancer from the human cytomegalovirus (hCMV IE1 promoter),
a synthetic 5'UTR including a Kozak sequence,
a murine immunoglobulin heavy chain signal sequence including the signal sequence intron (L1_intron_L2),
the cDNA for a heavy chain variable region (VH) arranged with a splice donor site at the 3' end,
the mouse Ig μ-enhancer region,
a human immunoglobulin heavy chain gamma 4-gene (IGHG4) including exons CH1, Hinge, CH2 and CH3, intervening introns and the 3'UTR bearing the polyadenylation signal sequence and optionally containing mutations,
an expression cassette for the expression of the human kappa-light chain comprising the following elements
the major immediate-early promoter and enhancer from the human cytomegalovirus (hCMV IE1 promoter),
a synthetic 5'UTR including a Kozak sequence,
a murine immunoglobulin heavy chain signal sequence including the signal sequence intron (L1_Intron_L2),
the cDNA for a light chain variable region arranged with a splice donor site at the 3' end (VL),
the intronic mouse Ig-kappa enhancer region,
a human immunoglobulin kappa gene (IGK) including the IGKC exon and the IGK 3'UTR bearing the polyadenylation signal sequence,
a Hygromycin B phosphotransferase transcription unit suitable for selection in eukaryotic cells including the SV40 early promoter and origin,
the hygromycin B phosphotransferase coding sequence (HygB),
the SV40 early polyadenylation signal,
an expression cassette for the expression of murine dihydrofolate reductase (DHFR) suitable for auxotrophic selection in eukaryotic cells including
a shortened version of the SV40 early promoter and origin,
the coding sequence for murine DHFR,
the SV40 early polyadenylation signal.
A plasmid map of p5031 is shown in FIG. 5.

Figure 6:
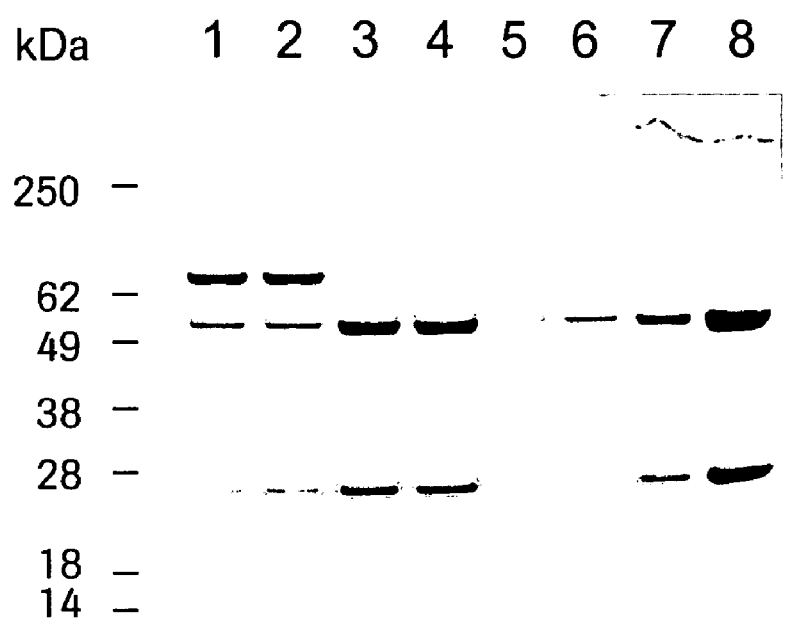
FIG. 6 SDS-PAGE analysis of antibodies secreted by HEK-293-EBNA cells after transfection with plasmid p5031 or p5032; Lanes 1+2: p5031, lanes 3+4: p5032, lanes 5–8: human anti-IGF-1R-antibody as reference antibody; 5: 0.2 µg, 6: 0.7 µg, 7: 2 µg, 8: 6 µg.

When HEK-293-EBNA cells were transfected with plasmid p5031, the cells produced immunoglobulins comprising an 80 kDa by-product (FIG. 6, lane 1 and 2). This protein was bound by anti-human Ig gamma-antibody as well as by anti-human Ig kappa-antibody in Western-Blot analysis.

EXAMPLE 5

Preparation of an Expression Plasmid for an Immunoglobulin of Class IgG4 with a Modified CH3-Domain The modification was introduced according to Example 3. In brief, T4565 was mutated to C together with a second nucleotide, T4559, which was also exchanged to C for removal of a BsmAI restriction site. Oligonucleotide 3

SEQ ID NO: 26
gcctctccct gtccctgggc aaatgagtgc cagg and oligonucleotide 4

SEQ ID NO: 27
cctggcactc atttgcccag ggacagggag aggc were used for the site-directed mutagenesis. The obtained plasmid was named p5032.

EXAMPLE 6

Expression of Nucleic Acids According to Example 5, Isolation of the Produced Immunoglobulin, and Analysis of the Produced Immunoglobulin Plasmids p5031 and p5032 were transiently transfected into HEK-293-EBNA cells. The cells were cultivated under non-selective conditions. After three days of cultivation the cell culture supernatants were harvested and the secreted immunoglobulins were purified with Protein A-Sepharose beads. Western blot analysis of the immunoglobulins with anti-human IgG-antibodies (H+L) showed that cells transfected with p5031 expressed a 80 kDa by-product (FIG. 6, lanes 1+2), whereas no by-product had been expressed by the cells transfected with p5032 (FIG. 6, lanes 3+4).

Plasmid p5032 was transfected into HEK-293-EBNA cells, the 80 kDa protein was not expressed (FIG. 6, lane 3 and 4). This clearly demonstrates that the 80 kDa fusion protein is a result of aberrant pre-mRNA splicing and that the production of such unwanted protein during transient expression can efficiently suppressed by the mutation of the internal CH3 splice site of the immunoglobulin heavy chain gamma 4 gene (IGHG4).

Figure 7:
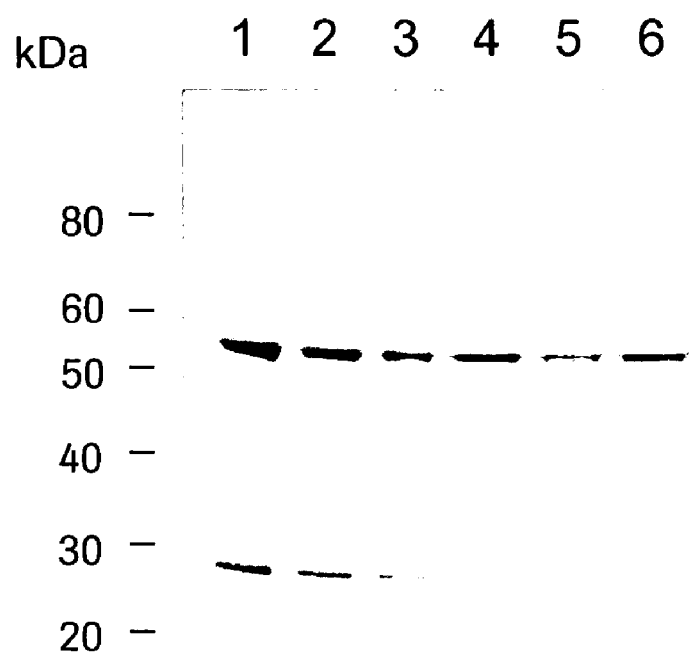
FIG. 7 CHO-DG44 cells transfected with p5032 and selected for stable integration of the plasmid with Methotrexate (MTX). Antibodies from six clones were purified and analyzed by SDS-PAGE and Coomassie staining.

Mutation of the internal $C_H3$ splice site of IGHG4 prevented the expression of the 80 kDa also in stable cell lines. CHO-DG44 cells were transfected with p5032 and selected for stable integration of the plasmid with Methotrexate (MTX). Antibodies from 6 clones were purified and analyzed by SDS-PAGE and Coomassie staining (FIG. 7). None of the antibodies contained the 80 kDa subunit.

The invention claimed is:

1. A nucleic acid encoding the amino acid sequence of the C-terminal part of the $C_H3$-domain of an immunoglobulin of the class IgA or IgG, or the amino acid sequence of the C-terminal part of the $C_H4$-domain of an immunoglobulin of the class IgE or IgM, wherein the glycine-lysine-dipeptide comprised in said amino acid sequence of the C-terminal part of the $C_H3$- or $C_H4$-domain is encoded by one of the following nucleic acid sequences, ggaaca, ggcaac, gggaaa, ggaaag, ggcaag, and gggaag, the nucleic acid ggaaaa, or the nucleic acid ggcaaa.

2. The nucleic acid of claim 1, wherein said nucleic acid encodes an amino acid sequence selected from the amino acid sequences of SEQ ID NO: 1, 3, 4, 5, 6, 7, or 8.

3. The nucleic acid of claim 2, wherein the nucleic acid encoding said glycine-lysine-dipeptide is preceded by the nucleotide g or a.

4. The nucleic acid of claim 3, wherein said glycine-lysine-dipeptide is encoded by the nucleic acid ggaaaa, or the nucleic acid ggcaaa, or the nucleic acid gggaaa.

5. The nucleic acid of claim 1, wherein the C-terminal part of the $C_H3$ domain, or the C-terminal part of the $C_H4$ domain, comprises at least the 20 C-terminal amino acids of the immunoglobulin heavy chain primary amino acid sequence.

6. The nucleic acid of claim 1, wherein said nucleic acid encodes a part of the C-terminal constant domain of an immunoglobulin heavy chain of the class IgA, IgE, IgM, or IgG and is selected from the nucleic acids of SEQ ID NO: 17, 18, 19, 20, 21, 22, 23, 30, or 31.

7. The nucleic acid of claim 6, wherein said nucleic acid is selected from the nucleic acids of SEQ ID NO: 17, 18, 19, 22, 23, 30, or 31.

8. The nucleic acid of claim 7, wherein nucleic acid is selected from the nucleic acids of SEQ ID NO: 17, 18, 19, 22, or 23.

9. The nucleic acid of claim 6, wherein said nucleic acid encodes a part of the C-terminal constant domain of a human immunoglobulin heavy chain of the class IgG1 or IgG4.

10. A plasmid comprising the nucleic acid of claim 1.

11. An isolated cell comprising the nucleic acid of claim 1, wherein said cell is a mammalian cell.

12. The cell of claim 11, characterized in that said mammalian cell is selected from a CHO cell, a HEK cell, or a BHK cell.

13. A nucleic acid comprising the nucleotide sequence of SEQ ID NO: 17, 18, 19, 20, 21, 22, 23, 30, or 31.

14. A nucleic acid of claim 13 comprising the nucleotide sequence of SEQ ID NO: 17, 18, 19, 22, or 23.

15. A method for the production of an immunoglobulin in a mammalian cell comprising the following steps:
   a) transfecting said mammalian cell with a nucleic acid encoding an immunoglobulin heavy chain, wherein a nucleic acid of SEQ ID NO: 17, 18, 19, 20, 21, 22, 23, 30, or 31 encodes the C-terminal part of the immunoglobulin heavy chain,
   b) cultivating the transfected mammalian cell under conditions suitable for the expression of the immunoglobulin,
   c) recovering the immunoglobulin from the culture or the cell.

16. The method of claim 15, wherein said mammalian cell is transfected with one nucleic acid comprising an expression cassette encoding an immunoglobulin heavy chain and an expression cassette encoding an immunoglobulin light chain.

17. The method of claim 15, wherein said mammalian cell is transfected with two nucleic acids, wherein the first nucleic acid comprises an expression cassette encoding an immunoglobulin light chain, and the second nucleic acid comprises an expression cassette encoding an immunoglobulin heavy chain.

18. The method of claim 16, wherein said transfecting said mammalian cell is with a nucleic acid encoding an immunoglobulin heavy chain, wherein a nucleic acid of SEQ ID NO: 17, 18, 19, 22, 23, 30, or 31 encodes the C-terminal part of the immunoglobulin heavy chain.

19. The method of claim 18, wherein said transfecting said mammalian cell is with a nucleic acid encoding an immunoglobulin heavy chain, wherein a nucleic acid of SEQ ID NO: 17, 18, 19, 22, or 23 encodes the C-terminal part of the immunoglobulin heavy chain.

20. A method for improving the expression of an immunoglobulin in a mammalian cell, comprising the following steps:
   a) transfecting a mammalian cell with a nucleic acid encoding an immunoglobulin heavy chain, wherein the nucleic acid encoding the immunoglobulin heavy chain comprises the nucleic acid ggaaaa, or the nucleic acid ggcaaa, or the nucleic acid gggaaa, or the nucleic acid ggaaag, or the nucleic acid ggcaag, or the nucleic acid gggaag encoding the glycine-lysine-dipeptide contained in the $C_H3$- or $C_H4$-domain of the immunoglobulin heavy chain,
   b) cultivating the transfected mammalian cell under conditions suitable for the expression of the immunoglobulin,
   c) recovering the immunoglobulin from the culture or the cell.

\* \* \* \* \*

SEQUENCE LISTING

<160> NUMBER OF SEQ ID NOS: 31

<210> SEQ ID NO 1
<211> LENGTH: 131
<212> TYPE: PRT
<213> ORGANISM: Homo sapiens

<400> SEQUENCE: 1

Gly Asn Thr Phe Arg Pro Glu Val His Leu Leu Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Glu Pro Ser
        50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala Gly
            100                 105                 110

Lys Pro Thr His Val Asn Val Ser Val Val Met Ala Glu Val Asp Gly
            115                 120                 125

Thr Cys Tyr
    130

<210> SEQ ID NO 2
<211> LENGTH: 109
<212> TYPE: PRT
<213> ORGANISM: Homo sapiens

<400> SEQUENCE: 2

Ala Ala Gln Ala Pro Val Lys Leu Ser Leu Asn Leu Leu Ala Ser Ser
1               5                   10                  15

Asp Pro Pro Glu Ala Ala Ser Trp Leu Leu Cys Glu Val Ser Gly Phe
            20                  25                  30

Ser Pro Pro Asn Ile Leu Leu Met Trp Leu Glu Asp Gln Arg Glu Val
            35                  40                  45

Asn Thr Ser Gly Phe Ala Pro Ala Arg Pro Pro Gln Pro Gly Ser
        50                  55                  60

Thr Thr Phe Trp Ala Trp Ser Val Leu Arg Val Pro Ala Pro Pro Ser
65                  70                  75                  80

Pro Gln Pro Ala Thr Tyr Thr Cys Val Val Ser His Glu Asp Ser Arg
                85                  90                  95

Thr Leu Leu Asn Ala Ser Arg Ser Leu Glu Val Ser Tyr
            100                 105

<210> SEQ ID NO 3
<211> LENGTH: 110
<212> TYPE: PRT
<213> ORGANISM: Homo sapiens

<400> SEQUENCE: 3

Gly Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe

```
                         20                  25                  30
Met Pro Glu Asp Ile Ser Val Gln Trp Leu His Asn Glu Val Gln Leu
            35                  40                  45

Pro Asp Ala Arg His Ser Thr Thr Gln Pro Arg Lys Thr Lys Gly Ser
 50                  55                  60

Gly Phe Phe Val Phe Ser Arg Leu Glu Val Thr Arg Ala Glu Trp Glu
 65                  70                  75                  80

Gln Lys Asp Glu Phe Ile Cys Arg Ala Val His Glu Ala Ala Ser Pro
                 85                  90                  95

Ser Gln Thr Val Gln Arg Ala Val Ser Val Asn Pro Gly Lys
            100                 105                 110

<210> SEQ ID NO 4
<211> LENGTH: 131
<212> TYPE: PRT
<213> ORGANISM: Homo sapiens

<400> SEQUENCE: 4

Gly Val Ala Leu His Arg Pro Asp Val Tyr Leu Leu Pro Pro Ala Arg
 1               5                  10                  15

Glu Gln Leu Asn Leu Arg Glu Ser Ala Thr Ile Thr Cys Leu Val Thr
            20                  25                  30

Gly Phe Ser Pro Ala Asp Val Phe Val Gln Trp Met Gln Arg Gly Gln
        35                  40                  45

Pro Leu Ser Pro Glu Lys Tyr Val Thr Ser Ala Pro Met Pro Glu Pro
 50                  55                  60

Gln Ala Pro Gly Arg Tyr Phe Ala His Ser Ile Leu Thr Val Ser Glu
 65                  70                  75                  80

Glu Glu Trp Asn Thr Gly Glu Thr Tyr Thr Cys Val Val Ala His Glu
                 85                  90                  95

Ala Leu Pro Asn Arg Val Thr Glu Arg Thr Val Asp Lys Ser Thr Gly
            100                 105                 110

Lys Pro Thr Leu Tyr Asn Val Ser Leu Val Met Ser Asp Thr Ala Gly
        115                 120                 125

Thr Cys Tyr
    130

<210> SEQ ID NO 5
<211> LENGTH: 107
<212> TYPE: PRT
<213> ORGANISM: Homo sapiens

<400> SEQUENCE: 5

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 6
<211> LENGTH: 107
<212> TYPE: PRT
<213> ORGANISM: Homo sapiens

<400> SEQUENCE: 6

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 7
<211> LENGTH: 107
<212> TYPE: PRT
<213> ORGANISM: Homo sapiens

<400> SEQUENCE: 7

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 8
<211> LENGTH: 107
<212> TYPE: PRT
<213> ORGANISM: Homo sapiens

<400> SEQUENCE: 8

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly

```
                65                  70                  75                  80
            Asn Val Phe Ser Cys Ser Val Met His Glu Ala Leu His Asn His Tyr
                            85                  90                  95
            Thr Gln Lys Ser Leu Ser Leu Ser Leu Gly Lys
                            100                 105

<210> SEQ ID NO 9
<211> LENGTH: 300
<212> TYPE: DNA
<213> ORGANISM: Homo sapiens

<400> SEQUENCE: 9
ggcttcagcc ccaaggacgt gctggttcgc tggctgcagg ggtcacagga gctgccccgc      60
gagaagtacc tgacttgggc atcccggcag gagcccagcc agggcaccac caccttcgct     120
gtgaccagca tactgcgcgt ggcagccgag gactggaaga agggggacac cttctcctgc     180
atggtgggcc acgaggccct gccgctggcc ttcacacaga gaccatcga ccgcttggcg      240 ggtaaaccca cccatgtcaa tgtgtctgtt gtcatggcgg aggtggacgg cacctgctac     300

<210> SEQ ID NO 10
<211> LENGTH: 300
<212> TYPE: DNA
<213> ORGANISM: Homo sapiens

<400> SEQUENCE: 10
taccacccaa cgtccgtgac tgtcacctgg tacatgggga cacagagcca gccccagaga      60
accttccctg agatacaaag acgggacagc tactacatga caagcagcca gctctccacc     120
cccctccagc agtggcgcca aggcgagtac aaatgcgtgg tccagcacac cgccagcaag     180
agtaagaagg agatcttccg ctggccaggt aggtcgcacc ggagatcacc cagaagggcc     240
ccccaggacc cccagcacct tccactcagg gcctgaccac aaagacagaa gcaagggctg     300

<210> SEQ ID NO 11
<211> LENGTH: 300
<212> TYPE: DNA
<213> ORGANISM: Homo sapiens

<400> SEQUENCE: 11
tttgcgacgc cggagtggcc ggggagccgg gacaagcgca ccctcgcctg cctgatccag      60
aacttcatgc ctgaggacat ctcggtgcag tggctgcaca acgaggtgca gctcccggac     120
gcccggcaca gcacgacgca gccccgcaag accaagggct ccggcttctt cgtcttcagc     180
cgcctggagg tgaccagggc cgaatgggag cagaaagatg agttcatctg ccgtgcagtc     240
catgaggcag cgagccctc acagaccgtc cagcgagcgg tgtctgtaaa tcccggtaaa      300

<210> SEQ ID NO 12
<211> LENGTH: 300
<212> TYPE: DNA
<213> ORGANISM: Homo sapiens

<400> SEQUENCE: 12
acgggcttct ctcccgcgga cgtcttcgtg cagtggatgc agaggggca gcccttgtcc       60 ccggagaagt atgtgaccag cgccccaatg cctgagcccc aggccccagg ccggtacttc     120
gcccacagca tcctgaccgt gtccgaagag gaatggaaca cgggggagac ctacacctgc     180
gtggtggccc atgaggccct gcccaacagg gtcaccgaga ggaccgtgga caagtccacc     240
ggtaaaccca ccctgtacaa cgtgtccctg gtcatgtccg acacagctgg cacctgctac     300
```

<210> SEQ ID NO 13
<211> LENGTH: 300
<212> TYPE: DNA
<213> ORGANISM: Homo sapiens

<400> SEQUENCE: 13
gtgtacaccc tgcccccatc ccgggatgag ctgaccaaga accaggtcag cctgacctgc     60
ctggtcaaag gcttctatcc cagcgacatc gccgtggagt gggagagcaa tgggcagccg    120
gagaacaact acaagaccac gcctcccgtg ctggactccg acggctcctt cttcctctac    180
agcaagctca ccgtggacaa gagcaggtgg cagcagggga acgtcttctc atgctccgtg    240
atgcatgagg ctctgcacaa ccactacacg cagaagagcc tctccctgtc tccgggtaaa    300

<210> SEQ ID NO 14
<211> LENGTH: 300
<212> TYPE: DNA
<213> ORGANISM: Homo sapiens

<400> SEQUENCE: 14
gtgtacaccc tgcccccatc ccgggaggag atgaccaaga accaggtcag cctgacctgc     60
ctggtcaaag gcttctaccc cagcgacatc gccgtggagt gggagagcaa tgggcagccg    120
gagaacaact acaagaccac acctcccatg ctggactccg acggctcctt cttcctctac    180
agcaagctca ccgtggacaa gagcaggtgg cagcagggga acgtcttctc atgctccgtg    240
atgcatgagg ctctgcacaa ccactacacg cagaagagcc tctccctgtc tccgggtaaa    300

<210> SEQ ID NO 15
<211> LENGTH: 300
<212> TYPE: DNA
<213> ORGANISM: Homo sapiens

<400> SEQUENCE: 15
gtgtacaccc tgcccccatc ccgggaggag atgaccaaga accaggtcag cctgacctgc     60
ctggtcaaag gcttctaccc cagcgacatc gccgtggagt gggagagcag cgggcagccg    120
gagaacaact acaacaccac gcctcccatg ctggactccg acggctcctt cttcctctac    180
agcaagctca ccgtggacaa gagcaggtgg cagcagggga acatcttctc atgctccgtg    240
atgcatgagg ctctgcacaa ccgcttcacg cagaagagcc tctccctgtc tccgggtaaa    300

<210> SEQ ID NO 16
<211> LENGTH: 300
<212> TYPE: DNA
<213> ORGANISM: Homo sapiens

<400> SEQUENCE: 16
gtgtacaccc tgcccccatc ccaggaggag atgaccaaga accaggtcag cctgacctgc     60
ctggtcaaag gcttctaccc cagcgacatc gccgtggagt gggagagcaa tgggcagccg    120
gagaacaact acaagaccac gcctcccgtg ctggactccg acggctcctt cttcctctac    180
agcaaggcta accgtggacaa gagcaggtgg caggagggga atgtcttctc atgctccgtg    240
atgcatgagg ctctgcacaa ccactacaca cagaagagcc tctccctgtc tctgggtaaa    300

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 17
ggcaaaccca cccatgtcaa tgtgtctgtt gtcatggcgg aggtggacgg cacctgctac    60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
catgaggcag cgagcccctc acagaccgtc cagcgagcgg tgtctgtaaa tcccggcaaa    60

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggcaaaccca ccctgtacaa cgtgtccctg gtcatgtccg acacagctgg cacctgctac    60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
atgcatgagg ctctgcacaa ccactacacg cagaagagcc tctccctgtc tccgggcaaa    60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atgcatgagg ctctgcacaa ccactacacg cagaagagcc tctccctgtc tccgggcaaa    60

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
atgcatgagg ctctgcacaa ccgcttcacg cagaagagcc tctccctgtc tccgggcaaa    60

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
```

```
atgcatgagg ctctgcacaa ccactacaca cagaagagcc tctccctgtc tctgggcaaa    60
```

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

```
agcctctccc tgtccccggg caaatgagtg cgacggccg                           39
```

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

```
cggccgtcgc actcatttgc ccggggacag ggagaggct                           39
```

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

```
gcctctccct gtccctgggc aaatgagtgc cagg                                34
```

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

```
cctggcactc atttgcccag ggacagggag aggc                                34
```

<210> SEQ ID NO 28
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
gggcagcccc gagaaccaca ggtgtacacc ctgcccccat cccgggatga gctgaccaag    60
aaccaggtca gcctgacctg cctggtcaaa ggcttctatc ccagcgacat cgccgtggag   120
tgggagagca atgggcagcc ggagaacaac tacaagacca cgcctcccgt gctggactcc   180
gacggctcct tcttcctcta cagcaagctc accgtggaca agagcaggtg gcagcagggg   240
aacgtcttct catgctccgt gatgcatgag gctctgcaca accactacac acagaagagc   300
ctctccctgt ctccgggtaa a                                             321
```

<210> SEQ ID NO 29

```
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gggcagcccc gagaaccaca ggtgtacacc ctgcccccat cccgggagga gatgaccaag      60
aaccaggtca gcctgacctg cctggtcaaa ggcttctacc ccagcgacat ctccgtggag     120
tgggagagca atgggcagcc ggagaacaac tacaagacca cacctcccat gctggactcc     180
gacggctcct tcttcctcta cagcaagctc accgtggaca agagcaggtg gcagcagggg     240
aacgtcttct catgctccgt gatgcatgag gctctgcaca accactacac gcagaagagc     300
ctctccctgt ctccgggtaa a                                              321

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
atgcatgagg ctctgcacaa ccactacaca cagaagagcc tctccctgtc tccgggcaaa      60

<210> SEQ ID NO 31
<211> LENGTH: 213
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
atctccgtgg agtgggagag caatgggcag ccggagaaca actacaagac cacacctccc      60
atgctggact ccgacggctc cttcttcctc tacagcaagc tcaccgtgga caagagcagg     120
tggcagcagg ggaacgtctt ctcatgctcc gtgatgcatg aggctctgca caaccactac     180
acgcagaaga gcctctccct gtctccgggc aaa                                 213
```